(12) United States Patent
Vazquez et al.

(10) Patent No.: US 6,515,024 B2
(45) Date of Patent: *Feb. 4, 2003

(54) SUCCINOYLAMINO HYDROXYETHYLAMINO SULFONYL UREA DERIVATIVES USEFUL AS RETROVIRAL PROTEASE INHIBITORS

(75) Inventors: Michael L. Vazquez, Gurnee, IL (US); Richard A. Mueller, Glencoe, IL (US); John J. Talley, Chesterfield, MO (US); Daniel P. Getman, Chesterfield, MO (US); Gary A. DeCrescenzo, St. Peters, MO (US); Eric T. Sun, San Diego, CA (US)

(73) Assignee: G. D. Searle & Co., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/011,778

(22) Filed: Dec. 11, 2001

(65) Prior Publication Data

US 2002/0198378 A1 Dec. 26, 2002

Related U.S. Application Data

(62) Division of application No. 08/542,861, filed on Oct. 13, 1995, now Pat. No. 6,337,398, which is a continuation of application No. 08/219,048, filed on Mar. 28, 1994, now abandoned, which is a continuation of application No. 07/969,682, filed on Oct. 30, 1992, now abandoned.

(51) Int. Cl.⁷ .................. A61K 31/18; C07C 311/00
(52) U.S. Cl. .......... 514/600; 514/183; 514/217.12; 514/237.8; 514/252.12; 514/331; 514/315; 514/428; 514/521; 514/542; 514/562; 540/483; 540/610; 544/159; 544/400; 546/233; 546/247; 548/568; 558/393; 560/13; 562/430; 564/79
(58) Field of Search .............. 564/79; 540/483, 540/610; 544/159, 400; 546/233, 247; 548/568; 514/183, 217.12, 237.8, 252.12, 331, 315, 428, 521, 542, 562, 600; 558/393; 560/13; 562/430

(56) References Cited

U.S. PATENT DOCUMENTS

| | | | |
|---|---|---|---|
| 4,450,164 A | 5/1984 | Bristol et al. | 424/256 |
| 4,477,441 A | 10/1984 | Boger et al. | 424/177 |
| 4,514,391 A | 4/1985 | Gordon et al. | 514/2 |
| 4,548,926 A | 10/1985 | Matsueda et al. | 514/19 |
| 4,599,198 A | 7/1986 | Hoover | 260/998.2 |
| 4,616,088 A | 10/1986 | Ryono et al. | 546/336 |
| 4,668,769 A | 5/1987 | Hoover | 530/331 |
| 4,668,770 A | 5/1987 | Boger et al. | 530/331 |
| 4,757,050 A | 7/1988 | Natarajan et al. | 514/18 |
| 4,880,938 A | 11/1989 | Freidinger | 548/492 |
| H725 H | 1/1990 | Gordon | 548/533 |
| 4,963,530 A | 10/1990 | Hemmi et al. | 514/19 |
| 4,977,277 A | 12/1990 | Rosenberg et al. | 549/215 |
| 5,521,219 A | 5/1996 | Vazquez et al. | 514/445 |
| 5,602,119 A * | 2/1997 | Vazquez et al. | 514/210 |

FOREIGN PATENT DOCUMENTS

| | | |
|---|---|---|
| AU | A-79823/87 | 4/1988 |
| EP | 104041 | 3/1984 |
| EP | 114993 | 8/1984 |
| EP | 172347 | 2/1986 |
| EP | 223437 | 5/1987 |
| EP | 0 264 795 | 4/1988 |
| EP | 337714 | 10/1989 |
| EP | 0 342 541 | 11/1989 |
| EP | 0 346 847 | 12/1989 |
| EP | 356223 | 2/1990 |
| EP | 389898 A2 | 10/1990 |
| EP | 389898 A3 | 10/1990 |
| EP | 393445 | 10/1990 |
| EP | 393457 | 10/1990 |
| EP | 402646 | 12/1990 |
| EP | 468641 | 1/1992 |
| GB | 2184730 | 7/1987 |
| GB | 2200115 | 7/1988 |
| GB | 2209752 | 5/1989 |
| WO | WO84/03044 | 8/1984 |
| WO | 92/08699 | 5/1992 |

OTHER PUBLICATIONS

Roberts et al, "Rational Design of Peptide–based Proteinase Inhibitors," Science, 248, 358 (1990).
Erickson et al, "Design Activity, and 2.8Å Crystal Structure of a $C_2$ Symmetric Inhibitor Complexed to HIV–1 Protease," Science, 249, 527 (1990).
Pearl et al, "Sequence specificity of retroviral proteases" Nature, 328, p. 482 (1987).
Martin, Drugs of the Future, 16(3), 210–212 (1991).
Meek et al. *Letter to Nature*, 343, 90–92 (1990).
McQuade et al, *Science*, 274, 454–456 (1990).
Rich et al, Peptide Inhibitors of Proteases, Proc.Am. Pept. Symp., 8th 511–520 (1983).
Rosenberg et al, *J. Med. Chem.*, 30, 1224–1228 (1987).
Miller et al, *Science*, 246, 1149 (1989).
Pauwles et al, *J. Virol Methods*, 20, 309–321 (1988).
Bundgaard, *Drugs Of The Future*, 16(5), p. 443–458 (1991).
Futtkau, *J. Prakt. Chem.*, 315, p. 1037 (1973).
Matier et al. *J. Med. Chem.* 15, No. 5, p. 539 (1972).

* cited by examiner

*Primary Examiner*—Richard L. Raymond
(74) *Attorney, Agent, or Firm*—Banner & Witcoff, Ltd.

(57) ABSTRACT

Succinoylamino hydroxyethylamino sulfonyl urea derivatives are effective as retroviral protease inhibitors, and in particular as inhibitors of HIV protease.

10 Claims, No Drawings

SUCCINOYLAMINO HYDROXYETHYLAMINO SULFONYL UREA DERIVATIVES USEFUL AS RETROVIRAL PROTEASE INHIBITORS

CROSS REFERENCE TO THE RELATED APPLICATIONS

This application is a division of application Ser. No. 08/542,861 filed Oct. 13, 1995, now U.S. Pat. No. 6,337,398 which was a continuation of application Ser. No. 08/219,048 filed on Mar. 28, 1994 (now abandoned), which was a continuation of application Ser. No. 07/969,682 filed Oct. 30, 1992 (now abandoned), all of which are invorporated herein by reference and on each of which the benefit of 35 U.S.C. 120 priority is claimed.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to derivatives of sulfamic acid-containing hydroxyethylamine protease inhibitor compounds, a composition and method for inhibiting retroviral proteases such as human immunodeficiency virus (HIV) protease and for treating a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition may involve a transition-state mimetic whereby the retroviral protease is exposed to a mimetic compound which binds to the enzyme in competition with the gag and gag-pol proteins to thereby inhibit replication of structural proteins and, more importantly, the retroviral protease itself. In this manner, retroviral replication proteases can be effectively inhibited.

Several classes of compounds have been proposed, particularly for inhibition of proteases, such as for inhibition of HIV protease. Such compounds include hydroxyethylamine isosteres and reduced amide isosteres. See, for example, EP O 346 847; EP O 342,541; Roberts et al, "Rational Design of Peptide-Based Proteinase Inhibitors, "Science, 248, 358 (1990); and Erickson et al, "Design Activity, and 2.8 Å Crystal Structure of a $C_2$ Symmetric Inhibitor Complexed to HIV-1 Protease," Science, 249, 527 (1990).

Several classes of compounds are known to be useful as inhibitors of the proteolytic enzyme renin. See, for example, U.S. Pat. No. 4,599,198; U.K. 2,184,730; G.B. 2,209,752; EP O 264 795; G.B. 2,200,115 and U.S. SIR H725. Of these, G.E. 2,200,115, GB 2,209,752, EP O 264,795, U.S. SIR H725 and U.S. Pat. No. 4,599,198 disclose urea-containing hydroxyethylamine renin inhibitors. G.B. 2,200,115 also discloses sulfamic acid-containing hydroxyethylamine renin inhibitors, and EP 0264 795 discloses certain sulfamic acid-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as derivatives of succinoylamino hydroxyethylamino sulfonyl urea inhibitor compounds.

DETAILED DESCRIPTION OF THE INVENTION

In accordance with the present invention, there is provided a retroviral protease inhibiting compound of the formula:

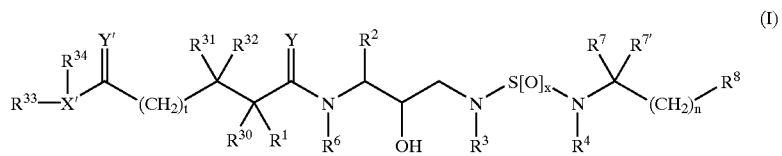

(I)

or a pharmaceutically acceptable salt, prodrug or ester thereof wherein:

$R^1$ represents hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyanoalanine and valine side chains;

$R^2$ represents alkyl, aryl, cycloalkyl, cycloalkylalkyl and aralkyl radicals, which radicals are optionally substituted with a group selected from alkyl and halogen radials, —NO$_2$, —CN, —CF$_3$, —OR$^9$ and —SR$^9$, wherein R$^9$ represents hydrogen and alkyl radicals;

R$^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof;

R$^4$ represents hydrogen and radicals as defined by R$^3$;

R$^6$ represents hydrogen and alkyl radicals;

R$^7$ and R$^{7'}$, independently represent hydrogen and radicals as defined for R$^3$, amino acid side chains selected from the group consisting of valine, isoleucine, glycine, alanine, allo-isoleucine, asparagine, leucine, glutamine, and t-butylglycine; radicals represented by the formulas —C(O)R$^{16}$, —CO$_2$R$^{16}$, —SO$_2$R$^{16}$, —SR$^{16}$, —CONR$^{16}$R$^{17}$, —CF$_3$ and —NR$^{16}$R$^{17}$; or R$^7$ and R$^{7'}$ together with the carbon atom to which they are attached form a cycloalkyl or heterocycloalkyl radical;

R$^8$ represents cyano, hydroxyl, alkyl, alkoxy, cycloalkyl, aryl, aralkyl, heterocycloalkyl and heteroaryl radicals and radicals represented by the formulas C(O)R$^{16}$, CO$_2$R$^{16}$, SO$_2$R$^{16}$, SR$^{16}$, CONR$^{16}$R$^{17}$, CF$_3$ and NR$^{16}$R$^{17}$;

wherein R$^{16}$ and R$^{17}$ independently represent hydrogen and radicals as defined for R$^3$, or R$^{16}$ and R$^{17}$ together with a nitrogen to which they are attached in the formula NR$^{16}$R$^{17}$ represent heterocycloalkyl and heteroaryl radicals;

R$^{30}$, R$^{31}$ and R$^{32}$ independently represent radicals as defined for R$^1$, or one of R$^1$ and R$^{30}$ together with one of R$^{31}$ and R$^{32}$ and the carbon atoms to which they are attached form a cycloalkyl radical;

R$^{33}$ and R$^{34}$ independently represent hydrogen and radicals as defined for R$^3$, or R$^{33}$ and R$^{34}$ together with X' represent cycloalkyl, aryl, heterocyclyl and heteroaryl radicals, provided that when X' is O, R$^{34}$ is absent;

x represents 1 or 2;

X' represents N, O and C(R$^{17}$) wherein R$^{17}$ represents hydrogen and alkyl radicals;

n represents an integer of from 0 to 6;

t represents 0, 1 or 2; and

Y and Y' independently represent O, S and NR$^{15}$ wherein R$^{15}$ represents hydrogen and radicals as defined for R$^3$.

Examples of compounds of the present invention as defined by Formula I include:

1) 4-[3-[[[[(1-carboxyethyl)amino]sulfonyl](2-methylpropyl)amino]-2R-hydroxy-1S-(phenylmethyl) propyl]amino]-2,2,3R-trimethyl-4-oxobutanoic acid
2) 4-[3-[[[[(1-carboxy-1-methylethyl)amino]sulfonyl](4-pyridinylmethyl)amino]-2R-hydroxy-1S-(phenylmethyl) propyl]amino]-3R-methyl-4-oxobutanoic acid
3) N-[[[3S-[(4-amino-2R,3,3-trimethyl-1,4-dioxobutyl) amino]-2R-hydroxy-4-phenylbutyl](3-methylbutyl) amino]sulfonyl]-2-methylalanine
4) 1-[[[3S-[(4-amino-2R,3,3-trimethyl-1,4-dioxobutyl) amino]-2R-hydroxy-4-phenylbutyl](3-methylbutyl) amino]sulfonyl]amino]cyclopentanecarboxylic acid
5) phenylmethyl-4-[2R-hydroxy-3-[[[(2-hydroxy-1,1-dimethylethyl)amino]sulfonyl](2-methylpropyl)amino]-1S-(phenylmethyl)propyl]-2,3R-dimethyl-4-oxobutanoate
6) 3-[[[[3S-[(4-amino-2R-methyl-1,4-dioxobutyl)amino]-2R-hydroxy-4-phenylbutyl](2-methylpropyl)amino] sulfonyl]amino]-3-methylbutanoic acid
7) phenylmethyl-4-[[3-[[[(1-carboxy-1-methylethyl) methylamino]sulfonyl](2-methylpropyl)amino]-2R-hydroxy-1S-(phenylmethyl)propyl]amino]-2,2,3R-trimethyl-4-oxobutanoate
8) 4-[[3-[[[(2-carboxypropyl)amino]sulfonyl](2-methylpropyl)amino]-2R-hydroxy-1S-(phenylmethyl) propyl]amino]-2,3R-dimethyl-4-oxobutanoic acid
9) 1-[[[(4-fluorophenyl)methyl][[3S-[2R-ethyl-3,3-dimethyl-1,4-dioxo-4-(phenylmethoxy)butyl]-2R-hydroxy-4-phenylbutyl]amino]sulfonyl]amino] cyclopropanecarboxylic acid
10) 1-[[[[2R-hydroxy-3S-[(4-methoxy-2R,3,3-trimethyl-1,4-dioxobutyl)amino]-4-phenylbutyl](3-methylbutyl) amino]sulfonyl]amino]cyclopropanecarboxylic acid A family of compounds of particular interest within Formula I are compounds embraced by Formula II:

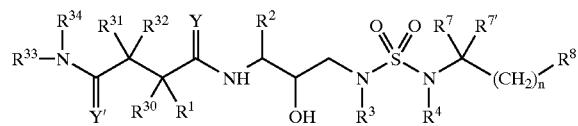

(II)

wherein

R$^1$ represents hydrogen, —CH$_2$SO$_2$NH$_2$, —CH$_2$CO$_2$CH$_3$, —CO$_2$CH$_3$, —CONH$_2$, —CH$_2$C(O) NHCH$_3$, —C(CH$_3$)$_2$(SH), —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals, and amino acid side chains selected from asparagine, S-methyl cysteine methionine and the sulfoxide (SO) and sulfone (SO$_2$) derivatives thereof, isoleucine, allo-isoleucine, alanine, leucine, tert-leucine, phenylalanine, ornithine, histidine, norleucine, glutamine, threonine, glycine, allo-threonine, serine, O-methyl serine, aspartic acid, beta-cyanoalanine and valine side chains;

R$^2$ represents alkyl, aryl, cycloalkyl, cycloalkylalkyl and aralkyl radicals, which radicals are optionally substituted with a group selected from alkyl and halogen radicals, —NO$_2$, —C≡N, CF$_3$, —OR$^9$, —SR$^9$, wherein R$^9$ represents hydrogen and alkyl radicals;

R$^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof;

R$^4$ represents hydrogen and radicals as defined by R$^3$;

R$^7$ and R$^{7'}$ independently represent radicals as defined for R$^3$ and amino acid side chains selected from the group consisting of valine, isoleucine, glycine, alanine, allo-isoleucine, asparagine, leucine, glutamine, and t-butylglycine or $R^7$ and $R^{7'}$ together with the carbon atom to which they are attached form a cycloalkyl radical;

$R^8$ represents cyano, hydroxyl, alkyl, alkoxy, cycloalkyl, aryl, aralkyl, heterocycloalkyl and heteroaryl radicals and radicals represented by the formulas $C(O)R^{16}$, $CO_2R^{16}$, $SO_2R^{16}$, $SR^{16}$, $CONR^{16}R^{17}$, $CF_3$ and $NR^{16}R^{17}$;

wherein $R^{16}$ and $R^{17}$ independently represent hydrogen and radicals as defined for $R^3$, or $R^{16}$ and $R^{17}$ together with a nitrogen to which they are attached in the formula $NR^{16}R^{17}$ represent heterocycloalkyl and heteroaryl radicals;

$R^{30}$, $R^{31}$ and $R^{32}$ independently represent radicals as defined for $R^1$, or one of $R^1$ and $R^{30}$ together with one of $R^{31}$ and $R^{32}$ and the carbon atoms to which they are attached form a cycloalkyl radical;

$R^{33}$ and $R^{34}$ independently represent hydrogen and radicals as defined for $R^3$, or $R^{33}$ and $R^{34}$ together with the nitrogen atom to which they are attached represent heterocycloalkyl and heteroaryl radicals;

n represents an integer of from 0 to 6; and

Y and Y' independently represent O, S and $NR^{15}$ wherein $R^{15}$ represents hydrogen and radicals as defined for $R^3$.

A more preferred family of compounds within Formula II consists of compounds wherein:

$R^1$ represents hydrogen and $CH_2C(O)NHCH_3$, $C(CH_3)_2(SCH_3)$, $C(CH_3)_2(S[O]CH_3)$, $C(CH_3)_2(S[O]_2CH_3)$, alkyl, alkenyl and alkynyl radicals, and amino acid side chains selected from the group consisting of asparagine, valine, threonine, allo-threonine, isoleucine, tert-leucine, S-methyl cysteine and methionine and the sulfone and sulfoxide derivatives thereof, alanine, and allo-isoleucine;

$R^2$ represents alkyl, cycloalkylalkyl and aralkyl radicals, which radicals are optionally substituted with halogen radicals and radicals represented by the formula $-OR^9$ and $-SR^9$ wherein $R^9$ represents alkyl radicals;

$R^3$ represents alkyl, haloalkyl, alkenyl, alkoxyalkyl, alkylthioalkyl, cycloalkyl, cycloalkylalkyl, heterocycloalkyl, heterocycloalkylalkyl, aryl, aralkyl and heteroaralkyl radicals;

$R^4$ represents hydrogen, alkyl, cycloalkyl, cycloalkylalkyl, aryl, heteroaryl, aralkyl, heteroaralkyl, heterocycloalkyl and heterocycloalkylalkyl radicals;

$R^7$ and $R^{7'}$ independently represent alkyl and aralkyl radicals or together with the carbon atom to which they re attached form a cycloalkyl radical having from 3 to 8 arbon atoms;

$R^8$ represents alkylcarbonyl, aryl, aroyl, aryloxy, aralkanoyl, cyano, hydroxycarbonyl, arylsulfonyl, alkylsulfonyl, alkylthio, hydroxyl, alkoxy, heteroaryl, dialkylaminocarbonyl, dialkylamino, cycloalkylamino, heterocyclylamino and alkoxycarbonyl radicals;

$R^{30}$, $R^{31}$ and $R^{32}$ independently represent hydrogen and alkyl, alkenyl and alkynyl radicals, or one of $R^1$ and $R^{30}$ together with one of $R^{31}$ and $R^{32}$ and the carbon atoms to which they are attached form a cycloalkyl radical;

$R^{33}$ and $R^{34}$ independently represent hydrogen and alkyl, alkenyl and alkynyl, hydroxyalkyl, alkoxyalkyl, cycloalkyl, cycloalkylalkyl, heterocycloalkyl, aryl, aralkyl, heteroaryl and heteroaralkyl radicals;

n is an integer of from 0 to 6; and

Y and Y' represent 0.

Of highest interest are compounds within Formula II wherein $R^1$ represents hydrogen and $CH_2C(O)NHCH_3$, $C(CH_3)_2(SCH_3)$, $C(CH_3)_2(S[O]CH_3)$, $C(CH_3)_2(S[O]_2CH_3)$, methyl, ethyl, propargyl, t-butyl, isopropyl and sec-butyl radicals, and amino acid side chains selected from the group consisting of asparagine, valine, S-methyl cysteine methionine, allo-iso-leucine, iso-leucine, and beta-cyano alanine side chains;

$R^2$ represents $CH_3SCH_2CH_2$—, iso-butyl, n-butyl, benzyl, 4-fluorobenzyl, 2-naphthylmethyl and cyclohexylmethyl radicals;

$R^3$ represents propyl, isoamyl, n-butyl, isobutyl, cyclohexyl, cyclohexylmethyl, benzyl and pyridylmethyl radicals;

$R^4$ represents hydrogen and methyl, ethyl, i-propyl, n-propyl, n-butyl, t-butyl, 1,1-dimethylpropyl and phenyl radicals;

$R^7$ and $R^{7'}$ independently represent methyl, ethyl, propyl and butyl radicals, or together with the carbon atom to which they are attached form a cyclopropyl, cyclobutyl, cyclopentyl or cyclohexyl radical;

$R^8$ represents methylcarbonyl, phenyl, hydroxy, methoxy, cyano, methoxycarbonyl, ethoxycarbonyl, isopropoxycarbonyl, t-butoxycarbonyl, benzyloxycarbonyl, carboxyl, methoxycarbonyl, methylsulfonyl, methylthio, phenylsulfonyl, phenyl, 2-, 3- or 4-pyridyl, 2-, 3- or 4-pyridyl N-oxide, N,N-dimethylamino, 1-piperidinyl, 4-morpholinyl, 4-(N-methyl)piperazinyl and 1-pyrrolidinyl;

$R^{30}$, $R^{31}$ and $R^{32}$ independently represent hydrogen and methyl, ethyl, propyl, butyl, pentyl and hexyl radicals, or one of $R^1$ and $R^{30}$ together with one of $R^{31}$ and $R^{32}$ form a cycloalkyl radical having from 3 to 8 carbon atoms;

$R^{33}$ and $R^{34}$ independently represent hydrogen, methyl, ethyl, propyl, isopropyl, butyl, isobutyl, tertiary butyl, pentyl and hexyl radicals, cyclohexylmethyl, cyclohexyl, benzyl and naphthylmethyl radicals;

n represents an integer of from 0 to 6; and

Y and Y' represent 0.

Another family of compounds of p articular interest within Formula I are compounds embraced by Formula III:

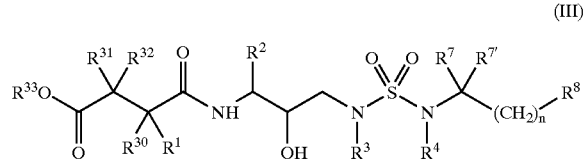

(III)

wherein:

$R^1$ represents hydrogen, $-CH_2SO_2NH_2$, $-CH_2CO_2CH_3$, $-CO_2CH_3$, $-CONH_2$, $-CH_2C(O)NHCH_3$, $-C(CH_3)(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

$R^2$ represents alkyl, aryl, cycloalkyl, cycloalkylalkyl and aralkyl radicals, which radicals are optionally substituted with a group selected from alkyl and halogen radicals, $-NO_2$, $-C\equiv N$, $CF_3$, $-OR^9$, $-SR^9$, wherein $R^9$ represents hydrogen and alkyl;

$R^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof;

$R^4$ represents hydrogen and radicals as defined for $R^3$;

$R^7$ and $R^{7'}$ independently represent radicals as defined for $R^3$ and amino acid side chains selected from the group consisting of valine, isoleucine, glycine, alanine, allo-isoleucine, asparagine, leucine, glutamine, and t-butylglycine or $R^7$ and $R^{7'}$ together with the carbon atom to which they are attached form a cycloalkyl radical;

$R^8$ represents cyano, hydroxyl, alkyl, alkoxy, cycloalkyl, aryl, aralkyl, heterocycloalkyl and heteroaryl radicals and radicals represented by the formulas $C(O)R^{16}$, $CO_2R^{16}$, $SO_2R^{16}$, $SR^{16}$, $CoNR^{16}R^{17}$, $CF_3$ and $NR^{16}R^{17}$;

wherein $R^{16}$ and $R^{17}$ independently represent hydrogen and radicals as defined for $R^3$, or $R^{16}$ and $R^{17}$ together with a nitrogen to which they are attached in the formula $NR^{16}R^{17}$ represent heterocycloalkyl and heteroaryl radicals;

$R^{30}$, $R^{31}$ and $R^{32}$ independently represent radicals as defined for $R^1$, or one of $R^1$ and $R^{30}$ together with one of $R^{31}$ and $R^{32}$ and the carbon atoms to which they are attached form a cycloalkyl radical;

$R^{33}$ represents hydrogen and radicals as defined for $R^3$; and n represents an integer of from 0 to 6.

A more preferred family of compounds within Formula III consists of compounds wherein $R^1$ represents hydrogen, alkyl, alkenyl and alkynyl radicals, and amino acid side chains selected from the group consisting of asparagine, valine, threonine, allo-threonine, isoleucine, tert-leucine, S-methyl cysteine methionine and the sulfone and sulfoxide derivatives thereof, alanine, and allo-isoleucine;

$R^2$ represents alkyl, cycloalkylalkyl and aralkyl radicals, which radicals are optionally substituted with halogen radicals and radicals represented by the formula $-OR^9$ and $-SR^9$ wherein $R^9$ represents hydrogen and alkyl and halogen radicals;

$R^3$ represents alkyl, haloalkyl, alkenyl, alkoxyalkyl, alkylthioalkyl, cycloalkyl, cycloalkylalkyl, heterocycloalkyl, heterocycloalkylalkyl, aryl, aralkyl, heteroaryl and heteroaralkyl radicals;

$R^4$ represents hydrogen, alkyl, cycloalkyl, cycloalkylalkyl, aryl, heteroaryl, aralkyl, heteroaralkyl, heterocycloalkyl and heterocycloalkylalkyl radicals;

$R^7$ and $R^{7'}$ independently represent radicals as defined for $R^3$ and amino acid side chains selected from the group consisting of valine, isoleucine, glycine, alanine, allo-isoleucine, asparagine, leucine, glutamine, and t-butylglycine or $R^7$ and $R^{7'}$ together with the carbon atom to which they are attached form a cycloalkyl radical;

$R^8$ represents cyano, hydroxyl, alkyl, alkoxy, cycloalkyl, aryl, aralkyl, heterocycloalkyl and heteroaryl radicals and radicals represented by the formulas $C(O)R^{16}$, $CO_2R^{16}$, $SO_2R^{16}$, $SR^{16}$, $CONR^{16}R^{17}$, $CF_3$ and $NR^{16}R^{17}$;

wherein $R^{16}$ and $R^{17}$ independently represent hydrogen and radicals as defined for $R^3$, or $R^{16}$ and $R^{17}$ together with a nitrogen to which they are attached in the formula $NR^{16}R^{17}$ represent heterocycloalkyl and heteroaryl radicals;

$R^{30}$, $R^{31}$ and $R^{32}$ independently represent hydrogen and alkyl, alkenyl and alkynyl radicals, or one of $R^1$ and $R^{30}$ together with one of $R^{31}$ and $R^{32}$ and the carbon atoms to which they are attached form a cycloalkyl radical;

$R^{33}$ represents hydrogen and alkyl, alkenyl and alkynyl, hydroxyalkyl, alkoxyalkyl, cycloalkyl, cycloalkylalkyl, heterocycloalkyl, aryl, aralkyl, heteroaryl and heteroaralkyl radicals; and n represents an integer of from 0 to 6.

Of highest interest are compounds within Formula III wherein $R^1$ represents hydrogen, methyl, ethyl, propargyl, t-butyl, isopropyl and sec-butyl radicals, and amino acid side chains selected from the group consisting of asparagine, valine, S-methyl cysteine methionine, allo-iso-leucine, iso-leucine, threonine, serine, aspartic acid, beta-cyano alanine, and allo-threonine side chains;

$R^2$ represents $CH_3SCH_2CH_2-$, iso-butyl, n-butyl, benzyl, 4-fluorobenzyl, 2-naphthylmethyl and cyclohexylmethyl radicals;

$R^3$ represents propyl, isobutyl, isoamyl, n-butyl, cyclohexyl, cyclohexylmethyl, benzyl and pyridylmethyl radicals;

$R^4$ represents hydrogen and methyl, ethyl, i-propyl, propyl, n-butyl, t-butyl, 1,1-dimethylpropyl and phenyl radicals, or $R^4$ and $R^5$ together with the nitrogen atom to which they are bonded form a pyrrolidinyl, piperidinyl, morpholinyl or piperazinyl radical;

$R^7$ and $R^{7'}$ independently represent methyl, ethyl, propyl and butyl radicals, or together with the carbon atom to which they are attached form a cyclopropyl, cyclobutyl, cyclopentyl or cyclohexyl radical;

$R^8$ represents methylcarbonyl, phenyl, hydroxy, methoxy, cyano, methoxycarbonyl, ethoxycarbonyl, isopropoxycarbonyl, t-butoxycarbonyl, benzyloxycarbonyl, carboxyl, methoxycarbonyl, methylsulfonyl, methylthio, phenylsulfonyl, phenyl, 2-, 3- or 4-pyridyl, 2-, 3- or 4-pyridyl N-oxide, N,N-dimethylamino, 1-piperidinyl, 4-morpholinyl, 4-(N-methyl)piperazinyl and 1-pyrrolidinyl.

$R^{30}$, $R^{31}$ and $R^{32}$ independently represent hydrogen and methyl, ethyl, propyl, butyl, pentyl and hexyl radicals, or one of $R^1$ and $R^{30}$ together with one of $R^{31}$ and $R^{32}$ form a cycloalkyl radical having from 3 to 8 carbon atoms;

$R^{33}$ represents hydrogen and methyl, ethyl, propyl, isopropyl, butyl, isobutyl, tertiary butyl, pentyl and hexyl radicals, cyclohexylmethyl, cyclohexyl, benzyl and naphthylmethyl radicals; and n represents an integer of from 0 to 6.

As utilized herein, the term "alkyl", alone or in combination, means a straight-chain or branched-chain alkyl radical containing from 1 to about 10, preferably from 1 to 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 18 carbon atoms preferably from 2 to 8 carbon atoms. Examples of suitable alkenyl radicals include ethenyl, propenyl, 1,4-butadienyl, 12-octadecene and the like. The term "alkynyl", alone or in combination, means a straight-chain hydrocarbon radical having one or more triple bonds and containing from 2 to about 10 carbon atoms, preferably from 2 to 8 carbon atoms. Examples of alkynyl radicals include ethynyl, propynyl, (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains from about 3 to about 8 carbon atoms and is cyclic. The term "cycloalkylalkyl" means an alkyl radical as defined above which is substituted by a cycloalkyl radical containing from about 3 to about 8, preferably from 3 to 6 carbon atoms. Examples of such cycloalkyl radicals include cyclopropyl, cyclobutyl, cyclopentyl, cyclohexyl and the like. The term "aryl", alone or in combination, means a phenyl or naphthyl radical which optionally carries one or more substituents selected from alkyl, alkoxy, halogen, hydroxy, amino, nitro, cyano, haloalkyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula —C(O)—O-aralkyl in which the term "aralkyl" has the significance given above. An example of an aralkoxycarbonyl radical is benzyloxycarbonyl. The term "aryloxy" means a radical of the formula aryl-O— in which the term aryl has the significance given above. The term "alkanoyl", alone or in combination, means an acyl radical derived from an alkanecarboxylic acid wherein alkane means a radical as defined above for alkyl. Examples of alkanoyl radicals include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl,2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl(hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclyalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e. =N—) by oxido and which is attached via a carbon atom. The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of heterocyclyl. Such heterocyclyl and heteroaryl radicals have from four to about 12 ring members, preferably from 4 to 10 ring members. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), guinoxalinyl, β-carbolinyl, 2-benzofurancarbonyl, 1-,2-,4- or 5-benzimidazolyl, and the like. The term "cycloalkylaikoxycarbonyl" means an acyl group derived from a cycloalkylalkoxycarboxylic acid of the formula cycloalkylalkyl-O—COOH wherein cycloalkylalkyl has the significance given above. The term "aryloxyalkanoyl" means an acyl radical of the formula aryl-O-alkanoyl wherein aryl and alkanoyl have the significance given above. The term "heterocyclyloxycarbonyl" means an acyl group derived from heterocyclyl-O—COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O—COOH wherein heterocyclyl has the significance given above. The term "heteroaryloxycarbonyl" means an acyl radical derived from a carboxylic acid represented by heteroaryl-O—COOH wherein heteroaryl has the significance given above. The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl" means an acyl group derived from an amino-substituted alkanecarboxylic acid wherein the amino group can be a primary, secondary or tertiary amino group containing substituents selected from hydrogen, and alkyl, aryl, aralkyl, cycloalkyl, cycloalkylalkyl radicals and the like. The term "halogen" means fluorine, chlorine, bromine or iodine. The term "haloalkyl" means an alkyl radical having the significance as defined above wherein one or more hydrogens are replaced with a halogen. Examples of such aloalkyl radicals include chloromethyl, 1-bromoethyl, fluoromethyl, difluoromethyl, trifluoromethyl, 1,1,1-trifluoroethyl and the like. The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R), which is the preferred stereochemistry for the compounds of the present invention. However, such procedures are generally applicable to those compounds of opposite configuration, e.g., where the stereochemistry about the hydroxyl group is (S). In addition, the compounds having the (R) stereochemistry can be utilized to produce those having the (S) stereochemistry. For example, a compound having the (R) stereochemistry can be inverted to the (S) stereochemistry using well-known methods.

Preparation of Compounds of Formula I

The compounds of the present invention represented by Formula I above can be prepared utilizing the following general procedure. This procedure is schematically shown in the following Schemes I and II:

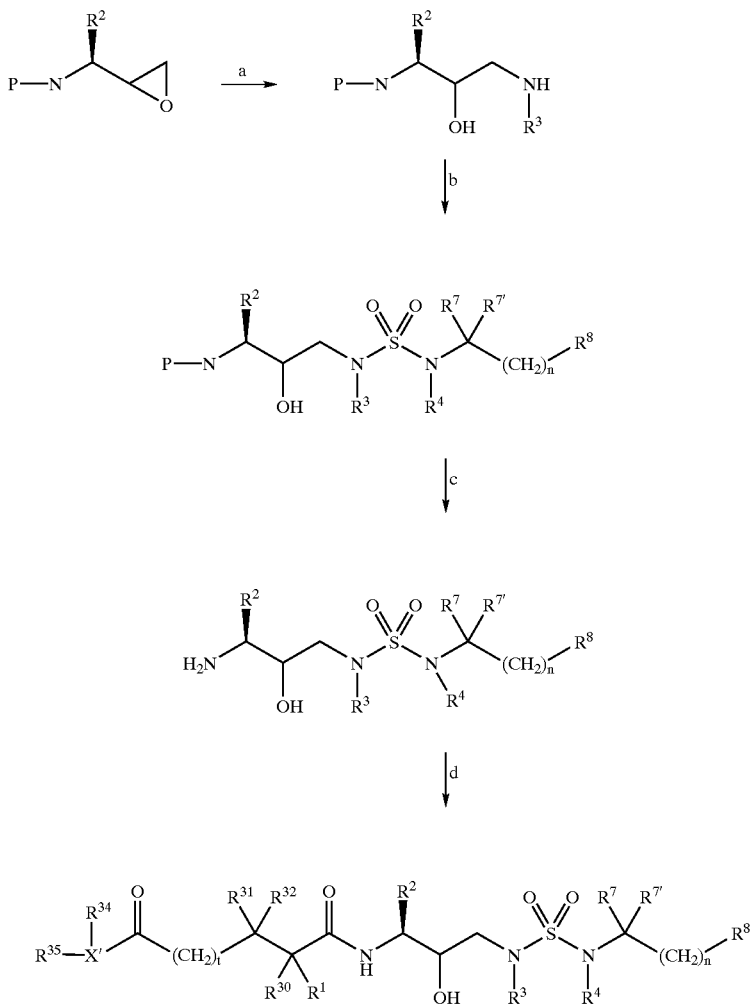

a) amine
b) sulfamoyl chloride $R^8(CH_2)_nC(R^7R^{7'})N(R^4)SO_2Cl$
   (or anhydride) + acid scavenger
c) deprotection
d) coupling

SCHEME II
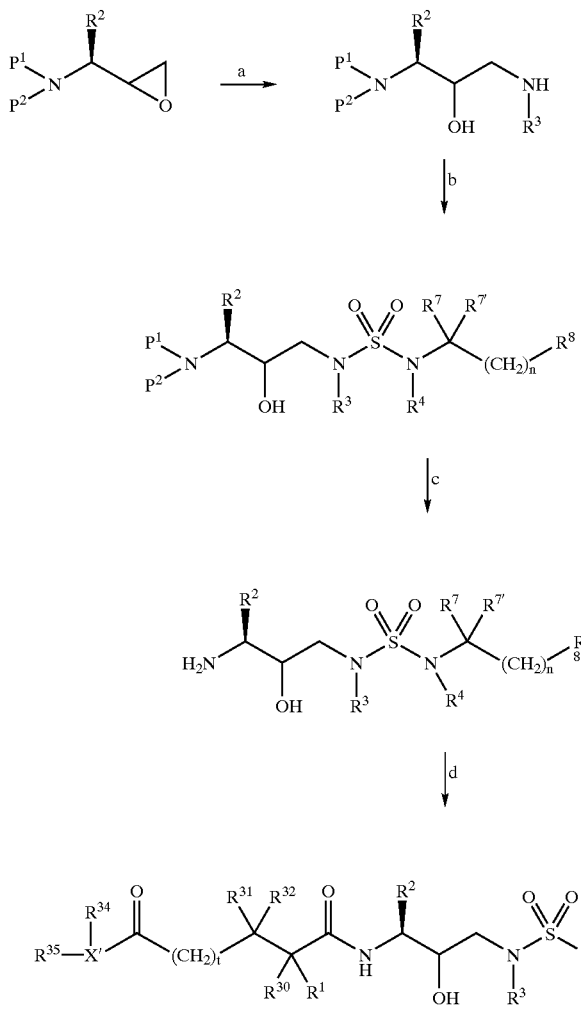
a) amine
b) sulfamoyl chloride $R^8(CH_2)nC(R^7R^{7'})N(R^4)SO_2Cl$
   (or anhydride) + acid scavenger
c) deprotection
d) coupling
SCHEME III
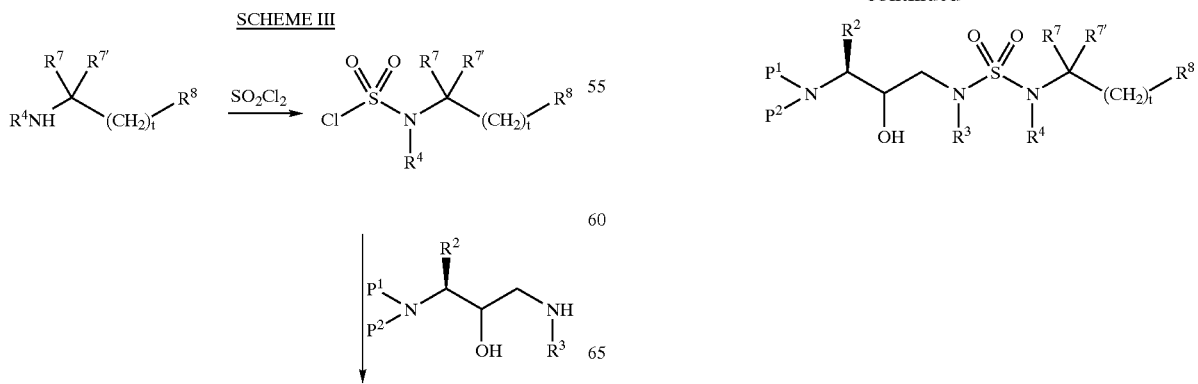

SCHEME IV

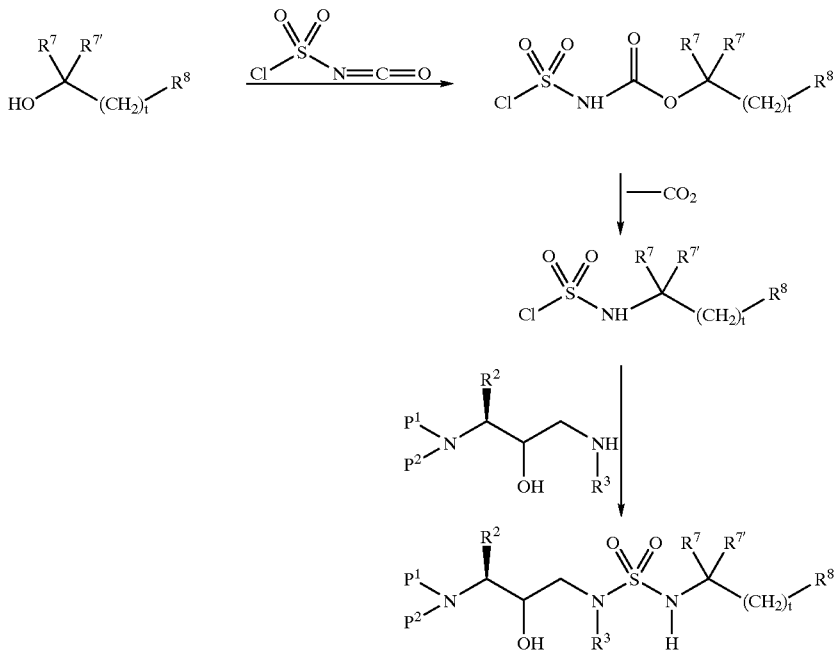

An N-protected chloroketone derivative of an amino acid having the formula:

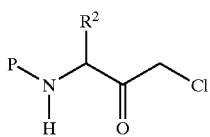

wherein P represents an amino protecting group, and $R^2$ is as defined above, is reduced to the corresponding alcohol utilizing an appropriate reducing agent. Suitable amino protecting groups are well known in the art and include carbobenzoxy, t-butoxycarbonyl, and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, tetrahydrofuran, and the like. The N-protected chloroketones are commercially available, e.g., such as from Bachem, Inc., Torrance, Calif. Alternatively, the chloroketones can be prepared by the procedure set forth in S. J. Fittkau, J. Prakt. Chem., 315, 1037 (1973), and subsequently N-protected utilizing procedures which are well known in the art.

The halo alcohol can be utilized directly, as described below, or, preferably, is then reacted, preferably at room temperature, with a suitable base in a suitable solvent system to produce an N-protected amino epoxide of the formula:

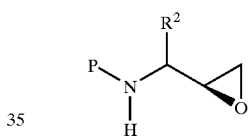

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared starting with an L-amino acid which is reacted with a suitable amino-protecting group in a suitable solvent to produce an amino-protected L-amino acid ester of the formula:

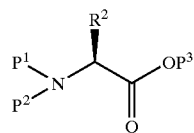

wherein $P^1$ and $P^2$ independently represent hydrogen, benzyl and amino-protecting groups (as defined above), provided that $P^1$ and $P^2$ are not both hydrogen; $P^3$ represents carboxyl-protecting group, e.g., methyl, ethyl, benzyl, tertiary-butyl and the like; and $R^2$ is as defined above.

The amino-protected L-amino acid ester is then reduced, to the corresponding alcohol. For example, the amino-protected L-amino acid ester can be reduced with diisobutylaluminum hydride at −78° C. in a suitable solvent such as toluene. The resulting alcohol is then converted, for example, by way of a Swern oxidation, to the corresponding aldehyde of the formula:

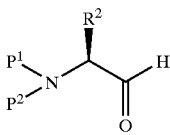

wherein $P^1$, $P^2$ and $R^2$ are as defined above. Thus, a dichloromethane solution of the alcohol is added to a cooled (−75 to −68° C.) solution of oxalyl chloride in dichloromethane and DMSO in dichloromethane and stirred for 35 minutes.

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Er or Cl. For example, a solution of the aldehyde and chloroiodomethane in THF is cooled to −78° C. and a solution of n-butyllithium in hexane is added. The resulting product is a mixture of diastereomers of the corresponding aminoprotected epoxides of the formulas:

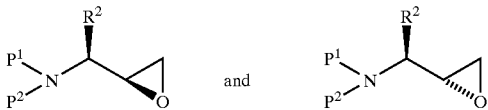

The diastereomers can be separated e.g., by chromatography, or, alternatively, once reacted in subsequent steps the diastereomeric products can be separated. For compounds having the (S) stereochemistry, a D-amino acid can be utilized in place of the L-amino acid.

The amino epoxide is then reacted, in a suitable solvent system, with an equal amount, or preferably an excess of, a desired amine of the formula:

$R^3NH_2$ wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic organic solvents such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. The resulting product is a 3-(N-protected amino)-3-($R^2$)-1-($NHR^3$)-propan-2-ol derivative (hereinafter referred to as an amino alcohol) can be represented by the formulas:

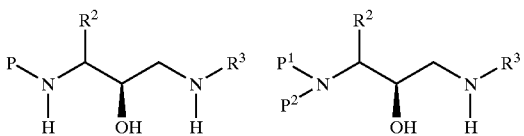

wherein P, $P^1$, $P^2$, $R^2$ and $R^3$ are as described above. Alternatively, a haloalcohol can be utilized in place of the amino epoxide.

The amino alcohol defined above is then reacted in a suitable solvent with a sulfamoyl halide, e.g. sulfamoyl chloride ($R^4R^5NSO_2Cl$ or $R^4HNSO_2Cl$) or sulfamoyl anhydride in the presence of an acid scavenger. Suitable solvents in which the reaction can be conducted include methylene chloride, tetrahydrofuran. Suitable acid scavengers include triethylamine, pyridine. The resulting sulfamic acid derivative can be represented, depending on the epoxide utilized, by the formulas:

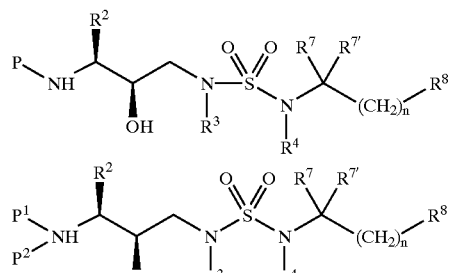

wherein p, $p^1$, $p^2$, $R^2$, $R^3$, $R^4$, $R^5$, $R^7$, $R^{7'}$, $R^8$ and n are as defined above. These intermediates are useful for preparing inhibitor compounds of the present invention and are also active inhibitors of retroviral proteases.

The sulfamoyl halides of the formula $[R^8(CH_2)_nC(R^7R^{7'})][R^4]NSO_2X$, wherein R4 is hydrogen can be prepared by the reaction of a suitable isocyanate of the formula $[R^8(CH_2)_nC(R^7R^{7'})][R^4]NCO$ with fuming sulfuric acid to produce the corresponding sulfamate which is then converted to the halide by well known procedures, such as by treating the sulfamate with $PCl_5$. Alternatively the isocyanate can be treated with chlorosulfonic acid to produce corresponding sulfamoyl chloride directly.

The sulfamoyl halides of the formula $[R^8(CH_2)_nC(R^7R^{7'})][R^4]NSO_2Cl$, wherein $R^4$ is other than hydrogen, can be prepared by reacting an amine of the formula $[R^8(CH_2)_nC(R^7R^{7'})][R^4]NH$, preferably as a salt such as the hydrochloride, with sulfuryl chloride in a suitable solvent such as acetonitrile. The reaction mixture is gradually warmed to reflux temperature and maintained at the reflux temperature until the reaction is complete. Alternatively, sulfamoyl halides of the formula $[R^8(CH_2)_nC(R^7R^{7'})][R^4]NSO_2Cl$ can be prepared by reacting an amine of the formula $[R^8(CH_2)_nC(R^7R^{7'})][R^4]NH$ with sulfuryl chloride in boiling MeCN as disclosed in Matier et al., *J. Med. Chem.*, 15, No. 5, p.538 (1972).

Alternatively, the sulfamoyl halide can be prepared by reacting a sulfamoyl halide derivative of an isocyanate, i.e., a derivative of the formula $ClSO_2NCO$ with an appropriate alcohol of the formula $HOC(R^7R^{7'})(CH_2)_nR^8$ to produce the corresponding compound of the formula $ClSO_2NHC(O)OC(R^7R^{7'})(CH_2)_nR^8$. Following deletion of the carbonyl moiety a sulfamoyl halide of the formula $ClSO2NHC(R^7R^{7'})(CH_2)_nR^8$ is produced. This procedure is described in *J. Org. Chem.*, 54, 5826–5828 (1989). Alternatively, the amino alcohol can be reacted with a chlorosulfonyl methyl ester of the formula $ClSO_2O$ alkyl to produce the corresponding derivative and then reacted with an amine of the formula $HNR^4R^5$.

Following preparation of the sulfonyl urea derivative, the amino protecting group P or $P^1$ and $P^2$ amino protecting groups are removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. Where the protecting group is a benzyl radical, it can be removed by hydrogenolysis. The resulting product is the amine salt derivative. Following neutralization of the salt, the amine is then reacted with a succinic acid, or derivative thereof, as described below, to produce the antiviral compounds of the present invention having the formula:

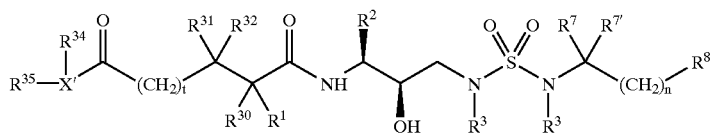

wherein t, $R^1$, $R^2$, $R^3$, $R^4$, $R^7$, $R^{7'}$, $R^8$, $R^{30}$, $R^{31}$, $R^{32}$, $R^{33}$ and $R^{34}$ are as defined above.

Alternatively, the protected amino alcohol from the epoxide opening can be further protected at the newly introduced amino group with a protecting group P' which is not removed when the first protecting P is removed. one skilled in the art can choose appropriate combinations of P and P'. one suitable choice is when P is Cbz and P' is Boc. The resulting compound represented by the formula:

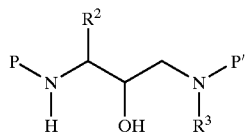

can be carried through the remainder of the synthesis to provide a compound of the formula:

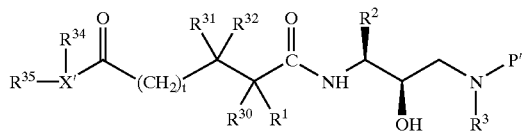

and the new protecting group P' is selectively removed, and following deprotection, the resulting amine reacted to form the sulfamic acid derivative as described above. This selective deprotection and conversion to the sulfamic acid can be accomplished at either the end of the synthesis or at any appropriate intermediate step if desired.

To produce the succinic acid portion of the compounds of Formula I, the starting material is a lactate of the formula:

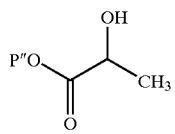

wherein P" represents alkyl and aralkyl radicals, such as, for example, ethyl, methyl, benzyl and the like. The hydroxyl group of the lactate is protected as its ketal by reaction in a suitable solvent system with methyl isopropenyl ether (1,2-methoxypropene) in the presence of a suitable acid. Suitable solvent systems include methylene chloride, tetrahydrofuran and the like as well as mixtures thereof. Suitable acids include $POCl_3$ and the like. It should be noted that well-known groups other than methyl isopropenyl ether can be utilized to form the ketal. The ketal is then reduced with diisobutylaluminum hydride (DIBAL) at −78° C. to produce the corresponding aldehyde which is then treated with ethylidene triphenylphosphorane (Wittig reaction) to produce a compound represented by the formula:

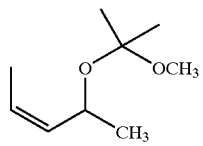

The ketal protecting group is then removed utilizing procedures well-known in the art such as by mild acid hydrolysis. The resulting compound is then esterified with isobutyryl chloride to produce a compound of the formula:

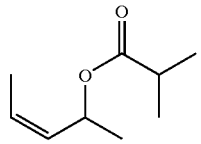

reaction mixture to room temperature to effect a Claisen rearrangement ([3,3]) to produce the corresponding acid represented by the formula:

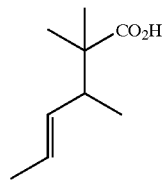

Those skilled in the art will recognize that variations on this scheme are possible, using either different protecting groups or reagents to carry out the same transformations. One can also utilize other acid chlorides in place of isobutyryl chloride to prepare similar analogs.

Treatment of the acid with benzyl bromide in the presence of a tertiary amine base, e.g., DBU, produces the corresponding ester which is then cleaved oxidatively to give a trisubstituted succinic acid:

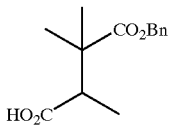

The trisubstituted succinic acid is then coupled to the sulfamate isostere utilizing procedures well known in the art. To produce the free acid, the benzyl ester is removed by hydrogenolysis to produce the corresponding acid. The acid can then be converted to the primary amide by methods well-known in the art. The resulting product is a compound represented by Formula I.

An alternative method for preparing trisubstituted succinic acids involves reacting an ester of acetoacetic acid represented by the formula:

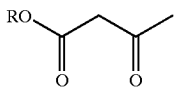

where R is a suitable protecting group, such as methyl, ethyl, benzyl or t-butyl with sodium hydride and a hydrocarbyl halide ($R^{31}X$ or $R^{32}X$) in a suitable solvent, e.g., THF, to produce the corresponding disubstituted derivative represented by the formula:

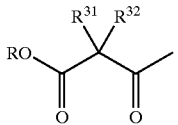

This disubstituted acetoacetic acid derivative is then treated with lithium diisopropyl amide at about −10° C. and in the presence of $PhN(triflate)_2$ to produce a vinyl triflate of the formula:

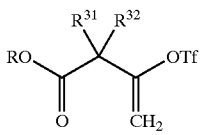

The vinyl triflate is then carbonylated utilizing a palladium catalyst, e.g., $Pd(OAc)_2$ and $Ph_3P$, in the presence of an alcohol (R"OH) or water (R"=H) and a base, e.g., triethylamine, in a suitable solvent such as DMF, to produce the olefinic ester or acid of the formula:

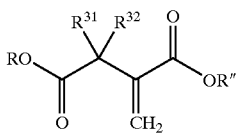

The olefin can then be subsequently asymmetrically hydrogenated, as described below, to produce a trisubstituted succinic acid derivative of the formula:

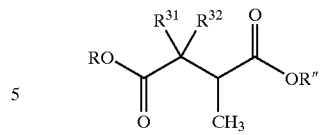

If R" is not H, R" can be removed by either hydrolysis, acidolysis, or hydrogenolysis, to afford the corresponding acid, which is then coupled to the sulfamate isostere as described above and then, optionally, the R group removed to produce the corresponding acid, and optionally, converted to the amide.

Alternatively, one can react the sulfamate isostere with either a suitably monoprotected succinic acid or glutaric acid of the following structure;

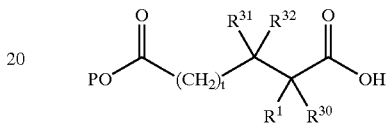

followed by removal of the protecting group and conversion of the resulting acid to an amide. One can also react an anhydride of the following structure;

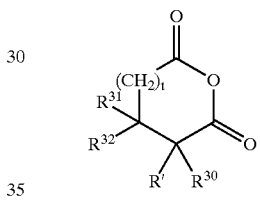

with the sulfamate isostere and then separate any isomers or convert the resulting acid to an amide and then separate any isomers.

It is contemplated that for preparing compounds of the Formulas having $R^6$, the compounds can be prepared following the procedure set forth above and, prior to coupling the sulfamate derivative or analog thereof, e.g. coupling to the amino acid $PNH(CH_2)_tCH(R^1)COOH$, carried through a procedure referred to in the art as reductive amination. Thus, a sodium cyanoborohydride and an appropriate aldehyde or ketone can be reacted with the sulfamate derivative compound or appropriate analog at room temperature in order to reductively aminate any of the compounds of Formulas I–IV. It is also contemplated that where $R^3$ of the amino alcohol intermediate is hydrogen, the inhibitor compounds of the present invention wherein $R^3$ is alkyl, or other substituents wherein the α-C contains at least one hydrogen, can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties, such as tautomers thereof as well as compounds, wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples 1 through 10 illustrate preparation of intermediates. These intermediates are useful in preparing the inhibitor compounds of the present invention.

EXAMPLE 1

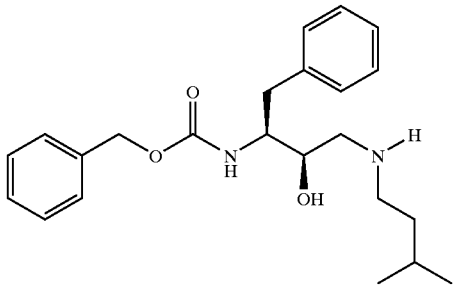

Preparation of N[3(S)-benzyloxycarbonylamino-2 (R)-hydroxy-4-phenylbutyl]-N-isoamylamine Part A To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150–151° C. and M+Li$^+$=340.

Part B

To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102–103° C. and MH$^+$ 298.

Part C

A solution of N-benzyloxycarbonyl 3(S)-amino-1,2-(S)-epoxy-4-phenylbutane (1.00 g, 3.36 mmol) and isoamylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3(S)-phenylmethylcarbamoyl)amino-2(R)-hydroxy-4-phenylbutyl]N-[(3-methylbutyl)]amine mp 108.0–109.5° C., MH$^+$ m/z=371.

EXAMPLE 2

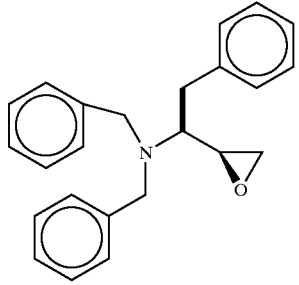

Preparation of N,N-dibenzyl-3(S)-amino-1,2-(S)-epoxy-4-phenylbutane

Step A

A solution of L-phenylalanine (50.0 g, 0.302 mol), sodium hydroxide (24.2 g, 0.605 mol) and potassium carbonate (83.6 g, 0.605 mol) in water (500 ml) is heated to 97° C. Benzyl bromide (108.5 ml, 0.912 mol) is then slowly added (addition time ~25 min). The mixture is then stirred at 97° C. for 30 minutes. The solution is cooled to room temperature and extracted with toluene (2×250 ml). The combined organic layers are then washed with water, brine, dried over magnesium sulfate, filtered and concentrated to give an oil product. The crude product is then used in the next step without purification.

Step B

The crude benzylated product of the above step is dissolved in toluene (750 ml) and cooled to −55° C. A 1.5 M solution of DIBAL-H in toluene (443.9 ml, 0.666 mol) is then added at a rate to maintain the temperature between −55° to −50° C. (addition time ~1 hour). The mixture is stirred for 20 minutes at −55° C. The reaction is quenched at −55° C. by the slow addition of methanol (37 ml). The cold solution is then poured into cold (5° C.) 1.5 N HCl solution (1.8 L). The precipitated solid (approx. 138 g) is filtered off and washed with toluene. The solid material is suspended in a mixture of toluene (400 ml) and water (100 ml). The mixture is cooled to 5° C., treated with 2.5 N NaOH (186 ml) and then stirred at room temperature until the solid is dissolved. The toluene layer is separated from the aqueous phase and washed with water and brine, dried over magnesium sulfate, filtered and concentrated to a volume of 75 ml (89 g). Ethyl acetate (25 ml) and hexane (25 ml) are then added to the residue upon which the alcohol product begins to crystallize. After 30 min., an additional 50 ml hexane is added to promote further crystallization. The solid is filtered off and washed with 50 ml hexane to give approximately 35 g of material. A second crop of material can be isolated by refiltering the mother liquor. The solids are combined and recrystallized from ethyl acetate (20 ml) and hexane (30 ml) to give, in 2 crops, approximately 40 g (40% from L-phenylalanine) of analytically pure alcohol product. The mother liquors are combined and concentrated (34 g). The residue is treated with ethyl acetate and hexane which provides an additional 7 g (~7% yield) of slightly impure solid product. Further optimization in the recovery from the mother liquor is probable.

Step C

A solution of oxalyl chloride (8.4 ml, 0.096 mol) in dichloromethane (240 ml) is cooled to −74° C. A solution of DMSO (12.0 ml, 0.155 mol) in dichloromethane (50 ml) is then slowly added at a rate to maintain the temperature at −74° C. (addition time ~1.25 hr). The mixture is stirred for 5 min. followed by addition of a solution of the alcohol (0.074 mol) in 100 ml of dichloromethane (addition time −20 min., temp. −75° C. to −68° C.). The solution is stirred at −78° C. for 35 minutes. Triethylamine (41.2 ml, 0.295 mol) is then added over 10 min. (temp. −78° to −68° C.) upon which the ammonium salt precipitated. The cold mixture is stirred for 30 min. and then water (225 ml) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde was carried on to the next step without purification.

Temperatures higher than −70° C. have been reported in the literature for the Swern oxidation. Other Swern modifications and alternatives to the Swern oxidations are also possible.

A solution of the crude aldehyde 0.074 mol and chloroiodomethane (7.0 ml, 0.096 mol) in tetrahydrofuran (285 ml) is cooled to −78° C. A 1.6 M solution of n-butyllithium in hexane (25 ml, 0.040 mol) is then added at a rate to maintain the temperature at −75° C. (addition time ~15 min.). After the first addition, additional chloroiodomethane (1.6 ml, 0.022 mol) is added again, followed by n-butyllithium (23 ml, 0.037 mol), keeping the temperature at −75° C. The mixture is stirred for 15 min. Each of the reagents, chloroiodomethane (0.70 ml, 0.010 mol) and n-butyllithium (5 ml, 0.008 mol) are added 4 more times over 45 min. at −75° C. The cooling bath is then removed and the solution warmed to 22° C. over 1.5 hr. The mixture is poured into 300 ml of saturated aq. ammonium chloride solution. The tetrahydrofuran layer is separated. The aqueous phase is extracted with ethyl acetate (1×300 ml). The combined organic layers are washed with brine, dried over magnesium sulfate, filtered and concentrated to give a brown oil (27.4 g). The product could be used in the next step without purification. The desired diastereomer can be purified by recrystallization at a subsequent step.

Alternately, the product could be purified by chromatography.

EXAMPLE 3

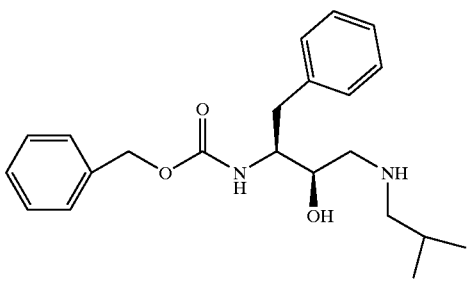

Preparation of N[3(S)-benzyloxycarbonylamino-2(R)-hydroxy-4-phenyl]N-isobutylamine A solution of N-benzyloxycarbonyl-3(S)-amino-1,2-(S)-epoxy-4-phenyl butane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N[3(S)-benzyloxycarbonylamino-2(R)-hydroxy-4-phenyl]N-isobutylamine, mp 108.0–109.5° C., MH+m/z=371.

EXAMPLE 4

Preparation of Sulfamoyl Chlorides

Method A

An amino acid ester hydrochloride (1 mmol) is suspended in a suitable solvent such as hexane, dichloromethane, toluene and the like, but most preferable acetonitrile. To the well stirred mixture is added sulfuryl chloride (3 mmol) in a suitable solvent, or neat, dropwise over several minutes. The reaction is allowed to stir at zero to reflux temperatures, preferable at reflux, for 1 to 48 hours, preferably for 24 hours. The solvent is removed and the residue triturated with a suitable solvent, such as hexane, pentane, toluene, but most preferably diethyl ether. The solvent is decanted and concentrated. The product may then be utilized as such or purified by distillation or in the case of solids recrystallized from appropriate solvents.

Method B

An alpha-hydroxy ester (1 mmol) is dissolved in an appropriate solvent such as acetonitrile, dichloromethane, toluene and the like, but most preferable hexane. Chlorosulfonyl isocyanate (1 mmol) added neat or in a solvent, preferably in hexane, is added dropwise. The reaction is stirred from zero to reflux, preferably at reflux, for 5 minutes to several hours, preferably for 1 hour. The solvent is then removed and the residue used as such, or taken up in an appropriate solvent, especially dichloromethane, and filtered to remove any impurities. The product may then be purified by distillation or in the case of solids recrystallized from appropriate solvents.

EXAMPLE 5

Preparation of Sulfamates

An amino alcohol as prepared in Example 3 (1 mmol) and a suitable base, such as triethylamine, pyridine, sodium carbonate, and the like, preferably diisopropylethylamine (1 mmol) are dissolved in a suitable solvent such as ether, chloroform, acetonitrile and the like, but preferably dichloromethane. The sulfamoyl chloride from part A or B of Example 4, neat or dissolved in an appropriate solvent, is added to the above solution. The reaction is stirred at zero to reflux temperatures, but preferably at room temperature for 1 to 48 hours. The product can be purified by silica gel chromatography or by an extractive workup followed by recrystallization.

EXAMPLE 6

Following the procedures of the previous Examples 1–5, the intermediate compounds set forth in Tables 1A and 1B could be prepared.

TABLE 1A

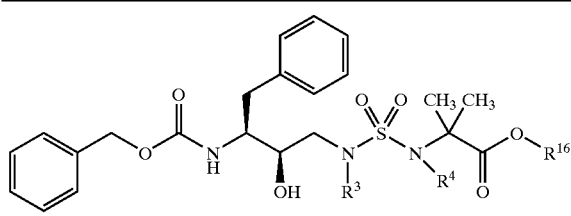

| $R^3$ | $R^{16}$ | $R^4$ |
|---|---|---|
| isobutyl | $CH_3$ | $CH_3$ |
| isoamyl | $CH_3$ | $CH_3$ |
| p-F benzyl | $CH_3$ | $CH_3$ |
| isobutyl | $CH_3$ | H |
| isobutyl | $CH_2CH_2CH_2CH_3$ | H |
| isobutyl | $CH(CH_3)_2$ | H |
| isobutyl | $C(CH_3)_3$ | H |
| isobutyl | $C_6H_5$ | H |

TABLE 1B

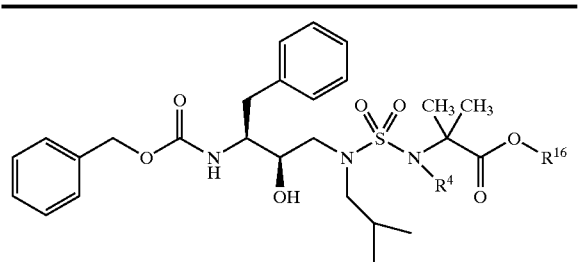

| Entry | $R^4$ | $R^{16}$ |
|---|---|---|
| 1 | $CH_3$ | $CH_3$ |
| 2 | H | $CH_3$ |
| 3 | H | $(CH_2)_3CH_3$ |
| 4 | H | $CH(CH_3)_2$ |
| 5 | H | $C(CH_3)_3$ |

The following Examples 7–10 illustrate preparation of succinoyl compounds. These intermediates can be coupled to the intermediate compounds of Examples 1–6 to produce inhibitor compounds of the present invention.

EXAMPLE 7

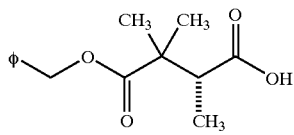

Preparation of Benzyl 2,2,3(R)-trimethylsuccinate

PART A

Preparation of Methyl (S)-lactate, 2-methoxy-2-propyl Ether

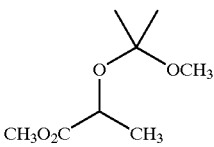

To a mixture of methyl(S)-(−)-lactate (13.2 g, 100 mmol) and, 2-methoxypropene (21.6 g, 300 mmol) in $CH_2Cl_2$ (150 ml) was added $POCl_3$ (7 drops) at r.t. and the resulting mixture was stirred at this temperature for 16 hours. After the addition of $Et_3N$ (10 drops), the solvents were removed in vacuo to give 20.0 g of (98%) desired product.

PART B

Preparation of 2(S)-hydroxypropanal, 2-methoxy-2-propyl Ether

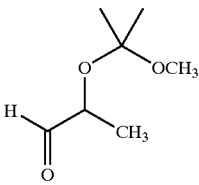

To a solution of compound from Part A (20.0 g) in $CH_2Cl_2$ (100 ml) was added DIBAL (65 ml of 1.5M solution in toluene, 97.5 mmol) dropwise at −78° C. for 45 min., then stirring was continued at this temperature for another 45 min. To this cold solution was added MeOH (20 ml), saturated NaCl solution (10 ml) and allowed the reaction mixture to warm up to r.t. and diluted with ether (200 ml), $MgSO_4$ (150 g) was added and stirred for another 2 h. The mixture was filtered and the solid was washed twice with ether. The combined filtrates were rotavaped to afford 11.2 g (78%) of the desired aldehyde.

PART C

Preparation of 2(S)-hydroxy-cis-3-butene, 2-methoxy-2-propyl Ether

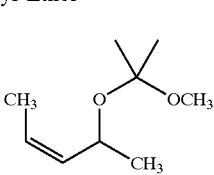

To a suspension of ethyltriphenylphosphonium bromide (28 g, 75.5 mmol) in THF (125 ml) was added $KN(TMS)_2$ (15.7 g, 95%, 75 mmol) in portions at 0° C. and stirred for 1 h at the temperature. This red reaction mixture was cooled to −78° C. and to this was added a solution of aldehyde from Part B (11 g, 75 mmol) in THF (25 ml). After the addition was completed, the resulting reaction mixture was allowed to warm up to r.t. and stirred for 16 h. To this mixture was added saturated NH₄Cl (7.5 ml) and filtered through a pad of celite with a thin layer of silica gel on the top. The solid was washed twice with ether. The combined filtrates were concentrated in vacuo to afford 11.5 g of crude product. The purification of crude product by flash chromatography (silica gel, 10:1 Hexanes/EtoAc) affording 8.2 g (69%) pure alkene.

PART D

Preparation of 2(S)-hydroxy-cis-3-butene

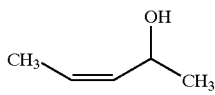

A mixture of alkene from Part C (8.2 g) and 30% aqueous acetic acid (25 ml) was stirred at r.t. for 1 hour. To this mixture was added NaHCO3 slowly until the pH was ~7, then extracted with ether (10×5). The combined ether solutions were dried (Na₂SO₄) and filtered. The filtrate was distilled to remove the ether to give 2.85 g (64%) pure alcohol, m/e=87(M+H).

PART E

Preparation of 2,2,3-trimethyl-hex-(trans)-4-enoic Acid

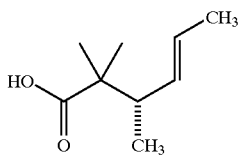

To a mixture of alcohol from Part D (2.5 g, 29 mmol) and pyridine (2.5 ml) in CH₂Cl₂ (60 ml) was added isobutyryl chloride (3.1 g, 29 mmol) slowly at 0° C. The resulting mixture was stirred at r.t. for 2 hours then washed with H₂O (30 ml×2) and sat. NaCl (25 ml). The combined organic phases were dried (Na₂SO₄), concentrated to afford 4.2 g (93%) ester 2(S)-hydroxy-cis-3-butenyl isobutyrate. This ester was dissolved in THF (10 ml) and was added to a 1.0M LDA soln. (13.5 ml of 2.0M LDA solution in THF and 13.5 ml of THF) slowly at −78° C. The resulting mixture was allowed to warm up to r.t. and stirred for 2 h and diluted with 5% NaOH (40 ml). The organic phase was separated, the aqueous phase was washed with Et₂O (10 ml). The aqueous solution was collected and acidified with 6N HCl to pH ~3. The mixture was extracted with ether (30 ml×3). The combined ether layers were washed with sat. NaCl (25 ml), dried (Na₂SO₄) and concentrated to afford 2.5 g (60%) of desired acid, m/e=157(M+H).

PART F

Preparation of benzyl 2,2,3(S)-trimethyl-trans-4-hexenoate

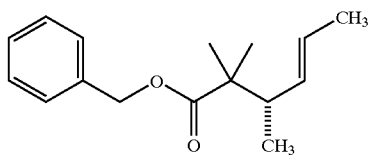

A mixture of acid from Part E (2.5 g, 16 mmol), BnBr (2.7 g, 15.8 mmol), K₂CO₃ (2.2 g, 16 mmol), NaI (2.4 g) in acetone (20 ml) was heated at 75° C. (oil bath) for 16 h. The acetone was stripped off and the residue was dissolved in H₂O (25 ml) and ether (35 ml). The ether layer was separated, dried (Na₂SO₄) and concentrated to afford 3.7 g (95%) of benzyl ester, m/e=247(M+H).

PART G

Preparation of Benzyl 2,2,3(R)-trimethylsuccinate

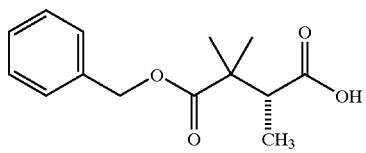

To a well-stirred mixture of KMnO₄ (5.4 g, 34, 2 mmol), H₂O (34 ml), CH₂Cl₂ (6 ml) and benzyltriethylammonium chloride (200 mg) was added a solution of ester from Part F (2.1 g, 8.54 mmol) and acetic acid (6 ml) in CH₂Cl₂ (28 ml) slowly at 0° C. The resulting mixture was stirred at the temperature for 2 h then r.t. for 16 h. The mixture was cooled in an ice-water bath, to this was added 6N HCl (3 ml) and solid NaHSO₃ in portions until the red color disappeared. The clear solution was extracted with CH₂Cl₂ (30 ml×3). The combined extracts were washed with sat. NaCl solution, dried (Na₂SO₄) and concentrated to give an oil. This oil was dissolved in Et₂O (50 ml) and to this was added sat. NaHCO₃ (50 ml). The aqueous layer was separated and acidified with 6N HCl to pH~3 then extracted with Et₂O (30 ml×3). The combined extracts were washed with sat. NaCl solution (15 ml), dried (Na₂SO₄) and concentrated to afford 725 mg (34%) of desired acid, benzyl 2,2,3(R)-trimethylsuccinate, m/e=251(M+H).

EXAMPLE 8

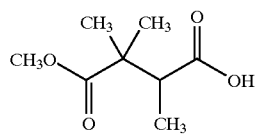

Preparation of Methyl 2,2-dimethyl-3-methyl Succinate, (R) and (S) Isomers

PART A

Preparation of Methyl 2,2-dimethyl-3-oxo-butanoate

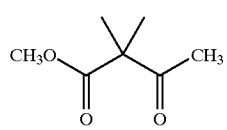

A 250 ml RB flask equipped with magnetic stir bar and N₂ inlet was charged with 100 ml dry THF and 4.57 g (180 mmol) of 95% NaH. The slurry was cooled to −20° C. and 10 g (87 mmol) methyl acetoacetate was added dropwise followed by 11.3 ml (181 mmol) CH₃I. The reaction was stirred at 0° C. for 2 hours and let cool to room temperature overnight. The reaction was filtered to remove NaI and diluted with 125 ml Et₂O. The organic phase was washed with 1×100 l 5% brine, dried and concentrated in vacuo to a dark golden oil that was filtered through a 30 g plug of silica gel with hexane. Concentration in vacuo yielded 10.05 g of desired methyl ester, as a pale yellow oil, suitable for use without further purification.

PART B

Preparation of Methyl 2,2-dimethyl-3-O-trifluoromethanesulfonate)-but-3-enoate

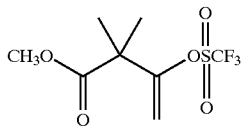

A 250 ml RB flask equipped with magnetic stir bar and N₂ inlet was charged with 80 mL by THF and 5.25 ml (37.5 mmol) diisopropylamine was added. The solution was cooled to −25° C. (dry ice/ethylene glycol) and 15 ml (37.5 mmol) of 2.5 M n-BuLi in hexanes was added. After 10 minutes a solution of 5 g 35 mmol) 1 in 8 ml dry THF was added. The deep yellow solution was stirred at −20° C. for 10 min. then 12.4 g N-phenyl bis(trifluoromethanesulfonimide) (35 mmol) was added. The reaction was stirred @ −10° C. for 2 hours, concentrated in vacuo and partioned between ethyl acetate and sat. NaHCO₃. The combined organic phase was washed with NaHCO₃, brine and conc. to an amber oil that was filtered through a 60 g silica gel plug with 300 mL 5% ethyl acetate/hexane. Conc. in vacuo yielded 9.0 g light yellow oil that was diluted with 65 ml ethyl acetate and washed with 2×50 ml 5% aq K2CO3, 1×10 mL brine, dried over Na₂SO₄ and conc. in vacuo to yield 7.5 g (87%) vinyl triflate, (m/e=277(M+H) suitable for use without further purification.

PART C

Preparation of Methyl 2,2-dimethyl-3-carboxyl-but-3-enoate

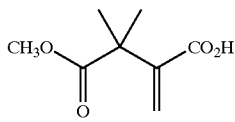

A 250 ml Fisher Porter bottle was charged with 7.5 g (27 mmol) of compound prepared in B, 50 ml dry DMF, 360 mg (1.37 mmol) triphenyl phosphine and 155 mg (0.69 mmol) Pd(II) (OAc)₂. The reaction mixture was purged twice with N₂ then charged with 30 psi CO. Meanwhile a solution of 20 ml dry DMF and 7.56 ml (54 mmol) NEt₃ was cooled to 0° C. to this was added 2.0 g (43 mmol) of 99% formic acid. The mixture was swirled and added to the vented Fisher Porter tube. The reaction vessel was recharged to 40 psi of CO and stirred 6 hours @ room temperature. The reaction mixture was concentrated in vacuo and partioned between 100 mL of ethyl acetate and 75 mL 5% aq K₂CO₃. The aqueous phase was washed with 1×40 mL additional ethyl acetate and then acidified with conc. HCl/ice. The aqueous phase was extracted with 2×70 mL of ethyl acetate and the organics were dried and conc. to yield 3.5 g (75%) white crystals, mp 72–75° C., identified as the desired product (m/e=173(M+H).

PART D

Preparation of Methyl 2,2-dimethyl-3-methylsuccinate, Isomer #1

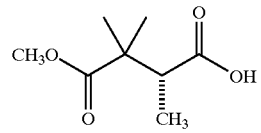

A steel hydrogenation vessel was charged with 510 mg (3.0 mmol) acrylic acid, from Part C, and 6 mg Ru (acac)₂ (R-BINAP) in 10 ml degassed MeOH. The reaction was hydrogenated at 50 psi/room temperature for 12 hours. The reaction was then filtered through celite and conc. to 500 mg clear oil which was shown to be a 93:7 mixture of isomer #1 and #2, respectively as determined by GC analysis using a 50 M β-cyclodextrin column: 150° C.–15 min. then ramp 2° C./min.; isomer #1, 17.85 min., isomer #2, 18–20 min.

PART E

Preparation of Methyl 2,2-dimethyl-3-methylsuccinate, Isomer #2

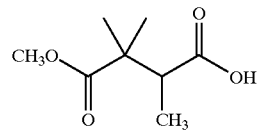

A steel hydrogenation vessel was charged with 500 mg (2.9 mmol) acrylic acid, Part C, and 6 mg Ru(OAc) (acac) (S-BINAP) in 10 ml degassed MeOH. The reaction was hydrogenated at 50 psi/room temperature for 10 hours. The reaction was filtered through celite and concentrated in vacuo to yield 490 mg of product as a 1:99 mixture of isomers #1 and #2, respectively, as determined by chiral GC as above.

In a similar manner, one can use benzyl 2,2-dimethyl-3-oxo-butanoate to prepare benzyl 2,2,3-trimethylsuccinate, R and S isomers. Other methods for preparing succinic acids, succinates and succinamides are well known in the art and can be utilized in the present invention.

EXAMPLE 9

Following the procedure generally as set forth in Examples 10 and 11, or utilizing methods well known in the art, the compounds shown in Tables 2 and 3 could be prepared.

TABLE 2

| $R^1$ | $R^{30}$ | $R^{31}$ | $R^{32}$ | X' | $R^{33}$ | $R^{34}$ |
|---|---|---|---|---|---|---|
| H | H | H | H | N | H | H |
| H | H | H | H | O | H | — |
| H | H | H | H | O | $CH_3$ | — |

TABLE 2-continued

R³⁴\X'—C(=O)—C(R³¹)(R³²)—C(R¹)(R³⁰)—C(=O)OH structure with R³³ on X'

| R¹ | R³⁰ | R³¹ | R³² | X' | R³³ | R³⁴ |
|---|---|---|---|---|---|---|
| CH₃ | H | H | H | N | H | H |
| CH₃ | H | H | H | O | H | — |
| H | H | CH₃ | H | N | H | H |
| H | H | CH₃ | H | O | H | — |
| CH₃ | CH₃ | H | H | N | H | H |
| CH₃ | CH₃ | H | H | O | H | — |
| CH₃ | CH₃ | H | H | O | CH₂C₆H₄OCH₃ | — |
| H | H | CH₃ | CH₃ | N | H | H |
| H | H | CH₃ | CH₃ | O | H | — |
| H | H | CH₃ | CH₃ | O | CH₂C₆H₄OCH₃ | — |
| CH₃ | H | CH₃ | H | N | H | H |
| CH₃ | H | CH₃ | H | N | H | CH₃ |
| CH₃ | H | CH₃ | H | N | CH₃ | CH₃ |
| CH₃ | H | CH₃ | H | O | H | — |
| CH₃ | H | CH₃ | H | N | H | —CH₂C₆H₅OCH₃ |
| OH | H | H | H | N | H | H |
| OH | H | H | H | O | H | — |
| H | H | OH | H | N | H | H |
| H | H | OH | H | O | H | — |
| CH₃ | H | H | H | N | H | H |
| CH₃ | H | H | H | O | H | — |
| CH₂C(O)NH₂ | H | H | H | N | H | H |
| CH₂C(O)NH₂ | H | H | H | O | H | — |
| CH₂C(O)NH₂ | H | H | H | O | CH₃ | — |
| CH₂Ph | H | H | H | N | H | H |
| CH₃ | H | CH₃ | CH₃ | N | H | H |
| CH₃ | H | CH₃ | CH₃ | O | H | — |
| CH₃ | H | CH₃ | CH₃ | N | H | CH₃ |
| CH₃ | H | CH₃ | CH₃ | N | CH₃ | CH₃ |

EXAMPLE 10

TABLE 3

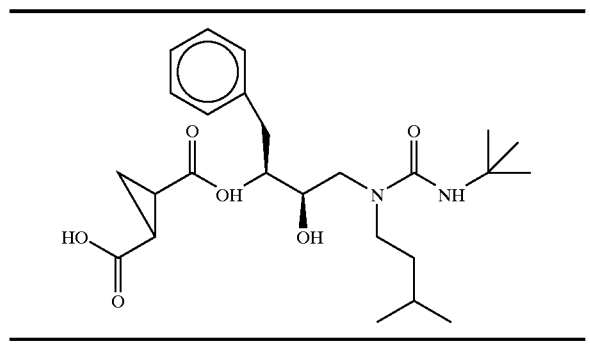

EXAMPLE 11

N[3(s)-benzyloxycarbonylamino-2 (R)-hydroxy-4-phenylbutyl]-N-isobutylamine (370 mg. 1.0 mmole), prepared as in Example 3, is mixed with DIEA (280 μL, 2.0 mmoles) and 1.0 mmole of the sulfamoyl chloride derivative of methyl aminoisobutyrate (2 mmol) in a 100 mL round bottomed flask equipped with a reflux condenser, nitrogen inlet, and magnetic stir bar. The slurry is warmed to reflux and maintained at this temperature for about 1 hour or is stirred at room temperature for about two days.

A solution of this product (1 mmole) containing 20 mL of methanol and 5 mL of acetic acid is hydrogenated over 10% palladium on carbon (80 mg) for 6 h.

The free amine (0.2 mmoles) is then coupled with 2,2-dimethyl-3-methylsuccinate (0.3 mmoles) in the presence of N-hydroxybenzotriazole (0.3 mmoles) and EDC (0.3 mmoles) to yield product.

Utilizing the procedures set forth above, the compounds shown in Tables 4–14 could be prepared. Thus, utilizing the intermediates of Examples 1–13 according to the procedures in Example 14, the compounds shown in Tables 4–16 could be prepared. General methods for preparing such compounds are set forth below.

General Procedure for the Synthesis of Amino Epoxide
Part A

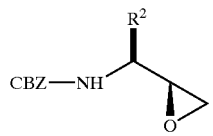

To a solution of 0.226 mol of N-benzyloxycarbonyl-L-amino acid chloromethyl ketone in a mixture of 807 mL of methanol and 807 mL of tetrahydrofuran at −2° C., is added 1.54 equiv. of solid sodium borohydride over one hundred minutes. The solvents are then removed under reduced pressure at 40° C. and the residue is dissolved in ethyl acetate (approx. 1 L). The solution is washed sequentially with 1M potassium hydrogen sulfate, saturated sodium bicarbonate and is then saturated sodium chloride solutions. After drying over anhydrous magnesium sulfate and filtering, the solution is removed under reduced pressure. To the resulting oil is added hexane (approx. 1 L) and the mixture is warmed to 60° C. with swirling. After cooling to room temperature, the solids are collected and washed with 2 L of hexane. The resulting solid is recrystallized from hot ethyl acetate and hexane to afford 32.3 g (43% yield) of N-benzyloxycarbonyl-3(S)-amino-1-chloro-4-phenyl-2(S)-butanol, mp 150–151° C. and M+Li$^+$=340.

Part B

To a solution of 1.2 equiv. of potassium hydroxide in 968 mL of absolute ethanol at room temperature, is added 0.097 mol of N-CBZ-3(S)-amino-1-chloro-4-substituted-2(S)-butanol. After stirring for fifteen minutes, the solvent is removed under reduced pressure and the solids are dissolved in methylene chloride. After washing with water, drying over magnesium sulfate, filtering and stripping, one obtains a white solid. Recrystallization from hot ethyl acetate and hexane will afford N-benzyloxycarbonyl-3(S)-amino-1,2(S)-epoxy-4-phenylbutane.

Alternate General Procedure for the Synthesis of Amino Epoxides

Step A

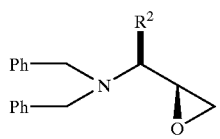

A solution of L-amino acid (0.302 mol), sodium hydroxide (24.2 g, 0.605 mol) and potassium carbonate (83.6 g, 0.605 mol) in water (500 ml) is heated to 97° C. Benzyl bromide (108.5 ml, 0.912 mol) is then slowly added (addition time ~25 min). The mixture is then stirred at 97° C. for 30 minutes. The solution is cooled to room temperature and extracted with toluene (2×250 ml). The combined organic layers are then washed with water, brine, dried over magnesium sulfate, filtered and concentrated to give an oil product. The crude product is then used in the next step without purification.

Step B

The crude benzylated product of the above step is dissolved in toluene (750 ml) and cooled to −55° C. A 1.5 M solution of DIBAL-H in toluene (443.9 ml, 0.666 mol) is then added at a rate to maintain the temperature between −55° to −50° C. (addition time ~1 hour). The mixture is stirred for 20 minutes at −55° C. The reaction is quenched at −55° C. by the slow addition of methanol (37 ml). The cold solution is then poured into cold (5° C.) 1.5 N HCl solution (1.8 L). The precipitated solid (approx. 138 g) is filtered off and washed with toluene. The solid material is suspended in a mixture of toluene (400 ml) and water (100 ml). The mixture is cooled to 5° C., treated with 2.5 N NaOH (186 ml) and then stirred at room temperature until the solid is dissolved. The toluene layer is separated from the aqueous phase and washed with water and brine, dried over magnesium sulfate, filtered and concentrated to a volume of 75 ml (89 g). Ethyl acetate (25 ml) and hexane (25 ml) are then added to the residue upon which the alcohol product begins to crystallize. After 30 min., an additional 50 ml hexane is added to promote further crystallization. The solid is filtered off and washed with 50 ml hexane to give approximately 35 g of material. A second crop of material can be isolated by refiltering the mother liquor. The solids are combined and recrystallized from ethyl acetate (20 ml) and hexane (30 ml) to give, in 2 crops, approximately 40 g of analytically pure alcohol product. The mother liquors are combined and concentrated (34 g). The residue is treated with ethyl acetate and hexane which provides an additional 7 g (~7% yield) of slightly impure solid product. Further optimization in the recovery from the mother liquor is probable.

Step C

A solution of oxalyl chloride (8.4 ml, 0.096 mol) in dichloromethane (240 ml) is cooled to −74° C. A solution of DMSO (12.0 ml, 0.155 mol) in dichloromethane (50 ml) is then slowly added at a rate to maintain the temperature at −74° C. (addition time ~1.25 hr). The mixture is stirred for 5 min. followed by addition of a solution of the alcohol (0.074 mol) in 100 ml of dichloromethane (addition time −20 min., temp. −75° C. to −68° C.). The solution is stirred at −78° C. for 35 minutes. Triethylamine (41.2 ml, 0.295 mol) is then added over 10 min. (temp. −78° to −68° C.) upon which the ammonium salt precipitated. The cold mixture is stirred for 30 min. and then water (225 ml) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde is carried on to the next step without purification.

Temperatures higher than −70° C. have been reported in the literature for the Swern oxidation. Other Swern modifications and alternatives to the Swern oxidations are also possible.

A solution of the crude aldehyde 0.074 mol and chloroiodomethane (7.0 ml, 0.096 mol) in tetrahydrofuran (285 ml) is cooled to −78° C. A 1.6 M solution of n-butyllithium in hexane (25 ml, 0.040 mol) is then added at a rate to maintain the temperature at −75° C. (addition time −15 min.). After the first addition, additional chloroiodomethane (1.6 ml, 0.022 mol) is added again, followed by n-butyllithium (23 ml, 0.037 mol), keeping the temperature at −75° C. The mixture is stirred for 15 min. Each of the reagents, chloroiodomethane (0.70 ml, 0.010 mol) and n-butyllithium (5 ml, 0.008 mol) are added 4 more times over 45 min. at −75° C. The cooling bath is then removed and the solution warmed to 22° C. over 1.5 hr.

The mixture is poured into 300 ml of saturated aq. ammonium chloride solution. The tetrahydrofuran layer is separated. The aqueous phase is extracted with ethyl acetate (1×300 ml). The combined organic layers are washed with brine, dried over magnesium sulfate, filtered and concentrated to give a brown oil (27.4 g). The product can be used in the next step without purification. The desired diastereomer can be purified by recrystallization at the subsequent sulfonamide formation step.

Alternately, the product can be purified by chromatography.

General Procedure for the Synthesis of 1,3-Diamino 4-phenyl Butan-2-ol Derivatives

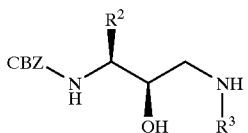

A mixture of the amine $R^3NH_2$ (20 equiv.) in dry isopropyl alcohol (20 mL/mmol of epoxide to be converted) is heated to reflux and then is treated with an N-Cbz amino epoxide of the formula:

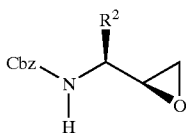

from a solids addition funnel over a 10–15 minute period. After the addition is complete the solution is maintained at reflux for an additional 15 minutes and the progress of the reaction monitored by TLC. The reaction mixture is then concentrated in vacuo to give an oil and is then treated with n-hexane with rapid stirring whereupon the ring opened-material precipitates from solution. Precipitation is generally complete within 1 hr and the product is then isolated by filtration on a Buchner funnel and is then air dried. The product is further dried in vacuo. This method affords amino alcohols of sufficient purity for most purposes.

General Procedure for the Reaction of Amino Alcohols with Sulfamoyl Halides: Preparation of Sulfamic Acids To a solution of N[3(S)-benzyloxycarbonylamino-2(R)-hydroxy-4-substituted] N-substituted amine (0.5 mmol) and a suitable amine (0.5 mmol) in dichloromethane (10 mL) is added (0.5 mmol) of the sulfamoyl chloride. The reaction mixture is stirred until the reaction is substantially complete, such as for 120 hours at room temperature, then the dichloromethane solution is concentrated and applied to a silica gel column (50 gm). The column is eluted with 2% methanol in dichloromethane, 1% ethanol and 1% methanol.

General Procedure for Preparation of Sulfamoyl Chlorides

To a solution of 547 mmol of sulfuryl chloride in 100 mL of anhydrous acetonitrile under a nitrogen atmosphere, was added 136 mmol of amine hydrochloride and the mixture heated to reflux for twenty-four to forty-eight hours. The solution was cooled and concentrated in vacuo to afford a semi-solid. Anhydrous diethyl ether was added, the solids removed by filtration are the filtrate concentrated to afford the crude sulfamoyl chloride. This can be used as is, or if desired, purified by either crystallization or distillation.

General Procedure for the Removal of the Protecting Groups by Hydroaenolysis with Palladium on Carbon A. Alcohol Solvent The Cbz-protected peptide derivative is dissolved in methanol (ca.20 mL/mmol) and 10% palladium on carbon catalyst is added under a nitrogen atmosphere.

The reaction vessel is sealed and flushed 5 times with nitrogen and then 5 times with hydrogen. The pressure is maintained at 50 psig for 1–16 hours and then the hydrogen is replaced with nitrogen and the solution is filtered through a pad of celite to remove the catalyst. The solvent is removed in vacuo to give the free amino derivative of suitable purity to be taken directly on to the next step.

B. Acetic Acid Solvent

The Cbz-protected peptide derivative is dissolved in glacial acetic acid (20 mL/mmol) and 10% palladium on carbon catalyst is added under a nitrogen atmosphere. The reaction vessel is flushed 5 times with nitrogen and 5 times with hydrogen and then maintained at 40 psig for about 2 h. The hydrogen is then replaced with nitrogen and the reaction mixture filtered through a pad of celite to remove the catalyst. The filtrate is concentrated and the resulting product is taken up in anhydrous ether and is evaporated to dryness 3 times. The final product, the acetate salt, is dried in vacuo and is of suitable purity for subsequent conversion.

General Procedure for Removal of Boc-protecting Group with 4N Hydrochloric Acid in Dioxane The Boc-protected amino acid or peptide is treated with a solution of 4N HCl in dioxane with stirring at room temperature. Generally the deprotection reaction is complete within 15 minutes, the progress of the reaction is monitored by thin layer chromatography (TLC). Upon completion, the excess dioxane and HCl are removed by evaporation in vacuo. The last traces of dioxane and HCl are best removed by evaporation again from anhydrous ether or acetone. The hydrochloride salt thus obtained is thoroughly dried in vacuo and is suitable for further reaction.

TABLE 4

| Entry | X | $R^3$ | $R^{16}$ |
|---|---|---|---|
| 1 | $NH_2$ | $CH_3$ | H |
| 2 | $NH_2$ | i-Butyl | $CH_3$ |
| 3 | $NH_2$ | i-Butyl | $CH_2CH_3$ |
| 4 | OH | i-Butyl | $CH(CH_3)_2$ |
| 5 | $NH_2$ | i-Propyl | $C(CH_3)_3$ |
| 6 | OH | i-Propyl | $CH_2Ph$ |
| 7 | $NH_2$ | $C_6H_5$ | H |
| 8 | $NH_2$ | —$CH_2$—cyclohexyl | $CH_3$ |
| 9 | $NH_2$ | —$CH_2$—phenyl | $C(CH_3)_3$ |
| 10 | OH | —$CH_2$—phenyl | H |
| 11 | $NH_2$ | cyclohexyl | $CH_2CH_3$ |
| 12 | $NH_2$ | i-Butyl | $C(CH_3)_3$ |
| 13 | OH | i-Butyl | H |
| 14 | OH | (R)—$CH(CH_3)$—phenyl | $CH_3$ |
| 15 | OH | $CH_2$—cyclohexyl | $CH_2CH_3$ |
| 16 | OH | —$CH_2$—cyclohexyl | $CH(CH_3)_2$ |

TABLE 4-continued

| Entry | X | R³ | R¹⁶ |
|---|---|---|---|
| 17 | OH | i-Butyl | C(CH₃)₃ |
| 18 | OH | i-Butyl | CH₂Ph |
| 19 | NH₂ | i-Butyl | H |
| 20 | NH₂ | i-Butyl | CH₃ |
| 21 | OH | —CH₂-cyclohexyl | C(CH₃)₃ |
| 22 | OH | (CH₂)₂CH(CH₃)₂ | H |
| 23 | NH₂ | i-Butyl | CH₂CH₃ |
| 24 | OH | i-Butyl | C(CH₃)₃ |
| 25 | NH₂ | i-Butyl | H |
| 26 | OH | —CH₂-naphthyl | CH₃ |
| 27 | NH₂ | —CH₂-naphthyl | CH₂CH₃ |
| 28 | OH | —(CH₂)₂CH(CH₃)₂ | CH(CH₃)₂ |
| 29 | NH₂ | —(CH₂)₂CH(CH₃)₂ | C(CH₃)₃ |
| 30 | OH | —CH₂C₆H₅ | CH₂Ph |
| 31 | NH₂ | —CH₂C₆H₅ | H |
| 32 | OH | —(CH₂)₂C₆H₅ | CH₃ |
| 33 | NH₂ | —(CH₂)₂C₆H₅ | C(CH₃)₃ |
| 34 | OH | n-Butyl | H |
| 35 | OH | n-Pentyl | CH₂CH₃ |
| 36 | OH | n-Hexyl | C(CH₃)₃ |
| 37 | OH | —CH₂-phenyl | H |
| 38 | OH | —CH₂C(CH₃)₃ | CH₂CH₂CH₂CH₃ |
| 39 | NH₂ | —CH₂C(CH₃)₃ | CH₂CH₂CH₂CH₃ |
| 40 | OH | —CH₂CH₂-morpholino | CH(CH₃)₂ |
| 41 | OH | —CH₂C₆H₅OCH₃ (para) | C(CH₃)₃ |
| 42 | OH | —CH₂-(3-pyridyl) | CH₂Ph |
| 43 | OH | —CH₂-(4-pyridyl) | H |
| 44 | OH | —(CH₂)₂C(CH₃)₃ | CH₃ |
| 45 | NH₂ | —(CH₂)₂C(CH₃)₃ | C(CH₃)₃ |
| 46 | OH | —(CH₂)₄OH | H |
| 47 | NH₂ | —(CH₂)₄OH | CH₂CH₃ |
| 48 | NH₂ | —CH₂-(4-F-phenyl) | C(CH₃)₃ |
| 49 | NH₂ | —CH₂-(4-pyridyl) | H |
| 50 | OCH₂Ph | —CH₂CH(CH₃)₂ | CH₃ |
| 51 | OCH₂Ph | —CH₂CH(CH₃)₂ | CH₂CH₃ |
| 52 | NH₂ | —CH₂CH(CH₃)₂ | CH(CH₃)₂ |
| 53 | OCH₂Ph | —CH₂CH(CH₃)₂ | C(CH₃)₃ |
| 54 | OH | —CH₂CH(CH₃)₂ | CH₂Ph |
| 55 | NH₂ | —CH₂CH(CH₃)₂ | H |
| 56 | OCH₂Ph | —CH₂CH(CH₃)₂ | CH₃ |
| 57 | OH | —CH₂CH(CH₃)₂ | C(CH₃)₃ |
| 58 | NH₂ | —CH₂CH(CH₃)₂ | H |
| 59 | OCH₂Ph | —CH₂CH(CH₃)₂ | CH₂CH₃ |
| 60 | OH | —CH₂CH(CH₃)₂ | C(CH₃)₃ |
| 61 | NH₂ | —CH₂CH(CH₃)₂ | H |
| 62 | OCH₂Ph | —CH₂CH(CH₃)₂ | CH₃ |
| 63 | OH | —CH₂CH(CH₃)₂ | CH₂CH₃ |
| 64 | NH₂ | —CH₂CH(CH₃)₂ | CH(CH₃)₂ |
| 65 | OCH₂Ph | —CH₂CH(CH₃)₂ | C(CH₃)₃ |
| 66 | OH | —CH₂CH(CH₃)₂ | CH₂Ph |
| 67 | NH₂ | —CH₂CH(CH₃)₂ | H |
| 68 | OCH₂Ph | —CH₂CH(CH₃)₂ | CH₃ |
| 69 | OH | —CH₂CH(CH₃)₂ | C(CH₃)₃ |
| 70 | NH₂ | —CH₂Ph | H |
| 71 | OCH₂Ph | —CH₂-(4-F-phenyl) | CH₂CH₃ |
| 72 | OH | —CH₂-cyclohexyl | C(CH₃)₃ |
| 73 | NH₂ | —CH₂-(4-OCH₃-phenyl) | H |
| 74 | OCH₂Ph | —CH₂-(3-pyridyl) | CH₃ |
| 75 | OH | —CH₂-cyclopropyl | H |
| 76 | NH₂ | —CH₂CH=CH₂ | CH₃ |
| 77 | OCH₂Ph | —CH₂-phenyl | CH₂CH₃ |

TABLE 4-continued

[Structure with X, CH₃, CH₃, O, CH₃, NH, OH, R³, N, S, O, O, NH, O, R¹⁶ groups, phenyl]

| Entry | X | R³ | R¹⁶ |
|---|---|---|---|
| 78 | OH | cyclohexyl | CH(CH₃)₂ |
| 79 | NH₂ | —CH₂CH₂Ph | C(CH₃)₃ |
| 80 | OCH₂Ph | —CH₂CH₂CH₂CH₂OH | CH₂Ph |
| 81 | OH | —CH₂CH₂N(CH₃)₂ | H |
| 82 | NH₂ | —CH₂CH₂—morpholinyl | CH₃ |
| 83 | OCH₂Ph | —CH₃ | C(CH₃)₃ |
| 84 | OH | —CH₂CH₂CH₂SCH₃ | H |
| 85 | NH₂ | —CH₂CH₂CH₂S(O)₂CH₃ | CH₂CH₃ |

TABLE 5

[Structure with HO, O, CH₃, CH₃, O, R¹, NH, OH, N, S, O, O, NH, O, OCH₂CH₃, isobutyl, phenyl groups]

| Entry | R¹ |
|---|---|
| 1 | CH₂SO₂CH₃ |
| 2 | (R)—CH(OH)CH₃ |
| 3 | CH(CH₃)₂ |
| 4 | (R,S)CH₂SOCH₃ |
| 5 | CH₂SO₂NH₂ |
| 6 | CH₂SCH₃ |
| 7 | CH₂CH(CH₃)₂ |
| 8 | CH₂CH₂C(O)NH₂ |
| 9 | (S)—CH(OH)CH₃ |
| 10 | —CH₂C≡CH |
| 11 | —CH₂CH₃ |
| 12 | —CH₂C(O)NH₂ |
| 13 | —C(CH₃)₂SO₂CH₃ |
| 14 | —CH₂CH=CH₂ |
| 15 | —C(CH₃)₂SCH₃ |

TABLE 6

[Structure with HO, O, CH₃, CH₃, O, R², NH, OH, N, S, O, O, NH, O, OCH₂CH₃, isopentyl groups]

| Entry | R² |
|---|---|
| 1 | n-Bu |
| 2 | cyclohexylmethyl |
| 3 | C₆H₅CH₂ |
| 4 | 2-naphthylmethyl |
| 5 | p-F(C₆H₄)CH₂ |
| 6 | p-(PhCH₂O)(C₆H₄)CH₂ |
| 7 | p-HO(C₆H₄)CH₂ |
| 8 | (CH₂)₂SCH₃ |

TABLE 7

[Structure with NH₂, O, CH₃, CH₃, O, NH, CH₃, OH, N, R³, S, O, O, NH, CH₃, CH₃, O, O, R¹⁶, phenyl groups]

| Entry | R³ | R¹⁶ |
|---|---|---|
| 1 | —CH₂CH(CH₃)₂ | —CH(CH₃)₂ |
| 2 | —CH₂CH(CH₃)₂ | cyclopropyl |
| 3 | —CH₂CH(CH₃)₂ | cyclobutyl |
| 4 | —CH₂CH(CH₃)₂ | cyclopentyl |
| 5 | —CH₂CH(CH₃)₂ | cyclohexyl |

TABLE 8

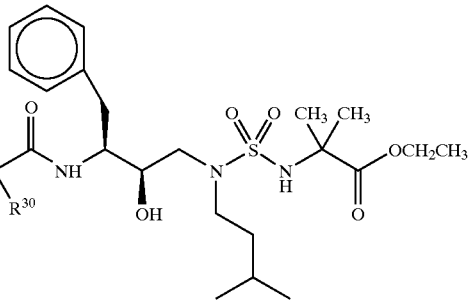

| Entry | R¹ | R³⁰ | R³¹ | R³² | X' | R³³ | R³⁴ |
|---|---|---|---|---|---|---|---|
| 1 | H | H | H | H | N | H | H |
| 2 | H | H | H | H | O | H | — |
| 3 | H | H | H | H | O | CH₃ | — |
| 4 | CH₃ | H | H | H | N | H | H |
| 5 | CH₃ | H | H | H | O | H | — |
| 6 | H | H | CH₃ | H | N | H | H |
| 7 | H | H | CH₃ | H | O | H | — |
| 8 | CH₃ | CH₃ | H | H | N | H | H |
| 9 | CH₃ | CH₃ | H | H | O | H | — |
| 10 | CH₃ | CH₃ | H | H | O | CH₂C₆H₄OCH₃ | — |
| 11 | H | H | CH₃ | CH₃ | N | H | H |
| 12 | H | H | CH₃ | CH₃ | O | H | — |
| 13 | H | H | CH₃ | CH₃ | O | CH₂C₆H₄OCH₃ | — |
| 14 | CH₃ | H | CH₃ | H | N | H | H |
| 15 | CH₃ | H | CH₃ | H | N | H | CH₃ |
| 16 | CH₃ | H | CH₃ | H | N | CH₃ | CH₃ |
| 17 | CH₃ | H | CH₃ | H | O | H | — |
| 18 | CH₃ | H | CH₃ | H | O | —CH₂C₆H₅OCH₃ | — |
| 19 | OH | H | H | H | N | H | H |
| 20 | OH | H | H | H | O | H | — |
| 21 | H | H | OH | H | N | H | H |
| 22 | H | H | OH | H | O | H | — |
| 23 | CH₂ | H | H | H | N | H | H |
| 24 | CH₂C(O)NH₂ | H | H | H | N | H | H |
| 25 | CH₂C(O)NH₂ | H | H | H | O | H | — |
| 26 | CH₂C(O)NH₂ | H | H | H | O | CH₃ | — |
| 27 | CH₂Ph | H | H | H | N | H | H |
| 28 | CH₃ | H | CH₃ | CH₃ | O | CH₂Ph | — |
| 29 | CH₃ | H | CH₃ | CH₃ | O | H | — |
| 30 | CH₃ | H | CH₃ | CH₃ | N | H | H |
| 31 | CH₃ | H | CH₃ | CH₃ | N | H | CH₃ |
| 32 | CH₃ | H | CH₃ | CH₃ | N | CH₃ | CH₃ |
| 33 | CH₂CH₃ | H | CH₃ | CH₃ | O | H | — |
| 34 | CH₂CH₃ | H | CH₃ | CH₃ | N | H | H |
| 35 | CH₃ | H | CH₂CH₃ | CH₂CH₃ | O | H | — |
| 36 | CH₃ | H | CH₂CH₃ | CH₂CH₃ | N | H | H |

TABLE 9

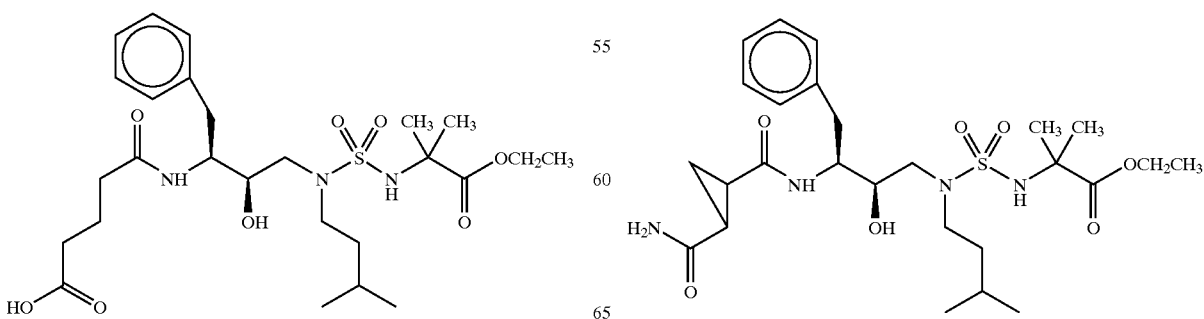

TABLE 9-continued

TABLE 9-continued
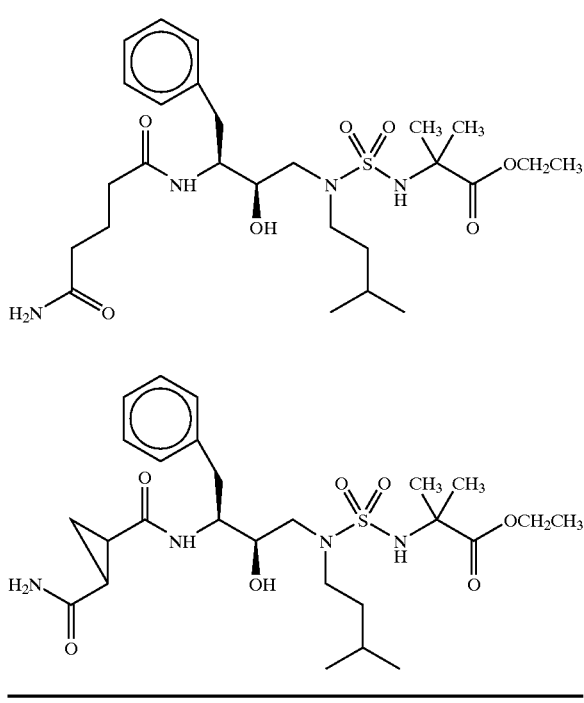
TABLE 10
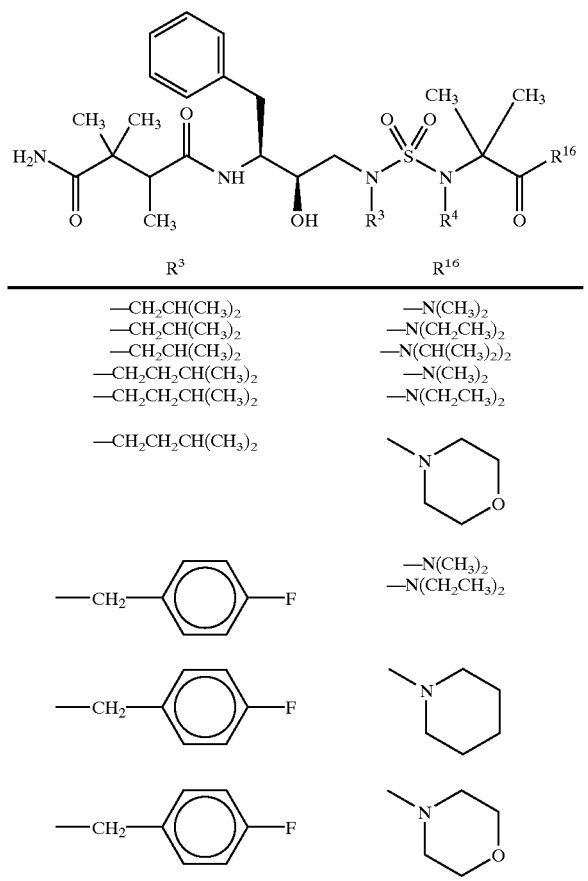
| R³ | R¹⁶ |
|---|---|
| —CH₂CH(CH₃)₂ | —N(CH₃)₂ |
| —CH₂CH(CH₃)₂ | —N(CH₂CH₃)₂ |
| —CH₂CH(CH₃)₂ | —N(CH(CH₃)₂)₂ |
| —CH₂CH₂CH(CH₃)₂ | —N(CH₃)₂ |
| —CH₂CH₂CH(CH₃)₂ | —N(CH₂CH₃)₂ |
| —CH₂CH₂CH(CH₃)₂ | 4-methylmorpholine |
| —CH₂-C₆H₄-F | —N(CH₃)₂, —N(CH₂CH₃)₂ |
| —CH₂-C₆H₄-F | 1-methylpiperidine |
| —CH₂-C₆H₄-F | 4-methylmorpholine |
TABLE 10-continued
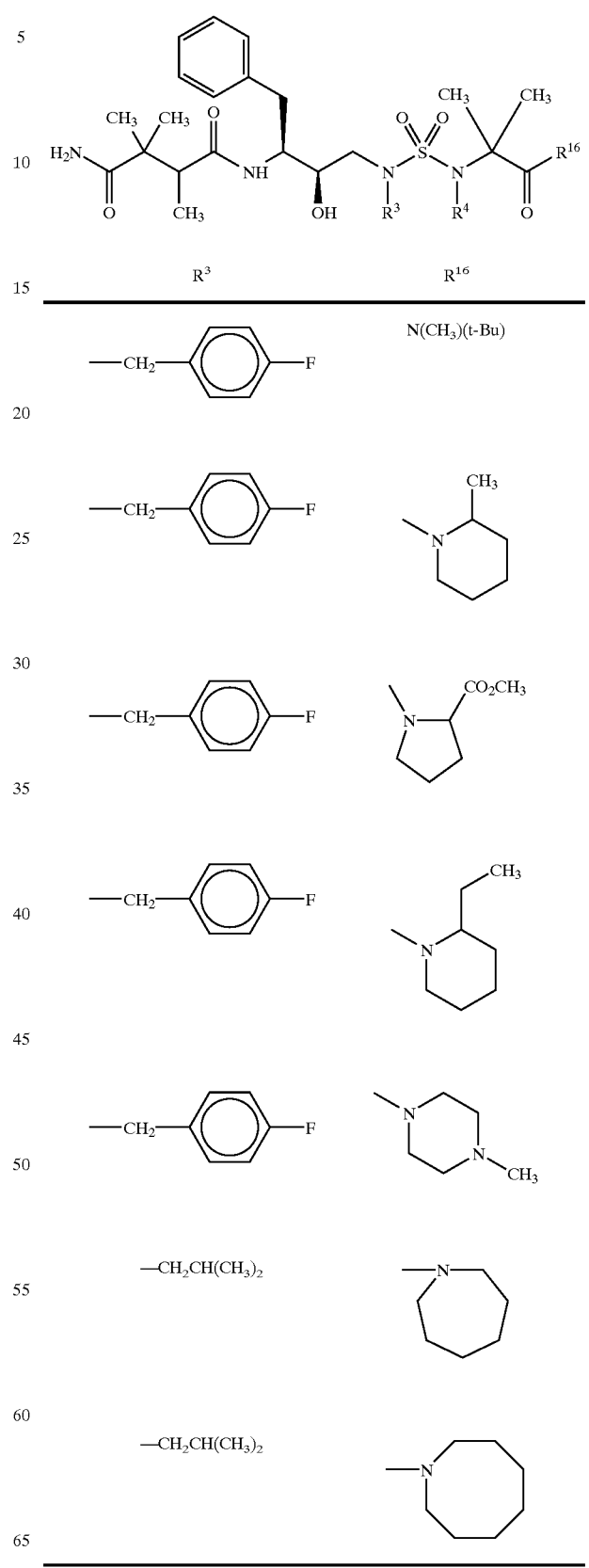

TABLE 11
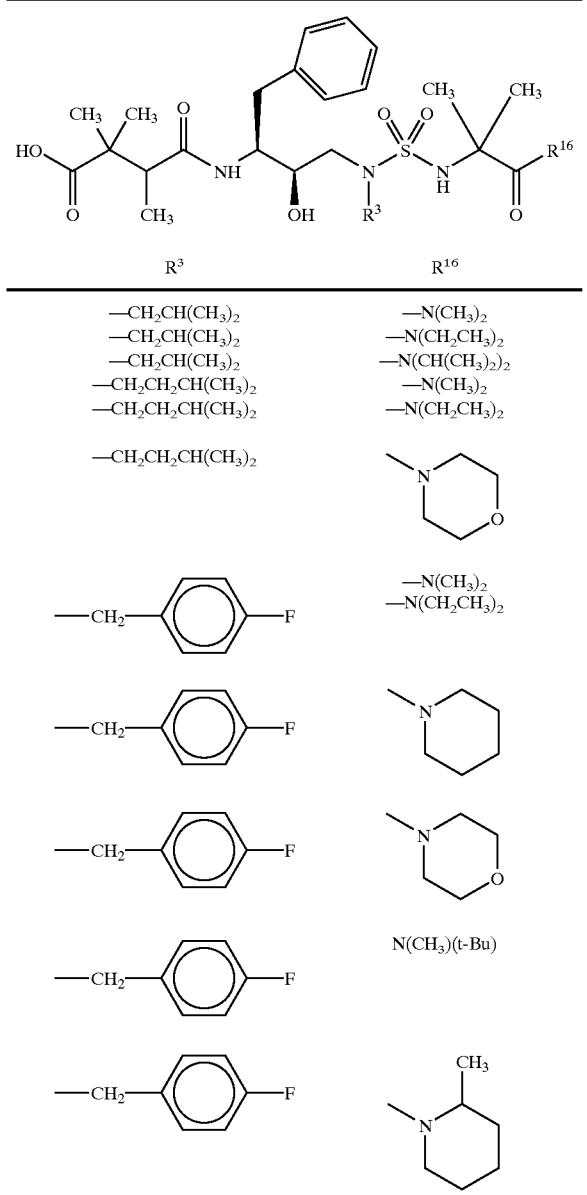
TABLE 11-continued
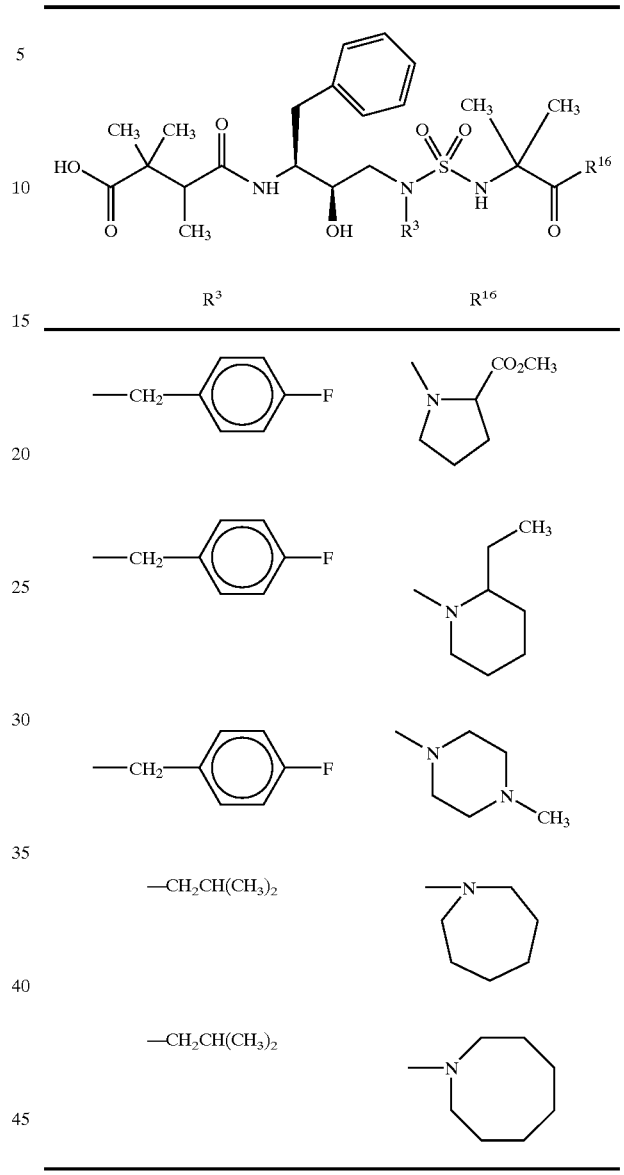
TABLE 12
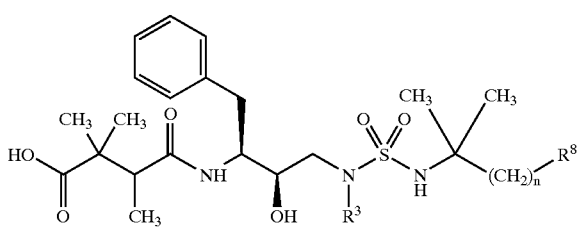

TABLE 12-continued
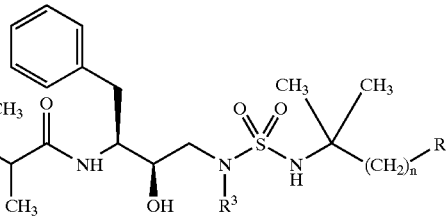
| n | R³ | R⁸ |
|---|---|---|
| 0 | —CH₂CH₂CH(CH₃)₂ | 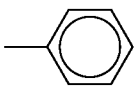 |
| 1 | —CH₂CH₂CH(CH₃)₂ | 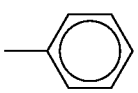 |
| 1 | —CH₂CH₂CH(CH₃)₂ | —C(O)N(CH₃)₂ |
| 1 | —CH₂CH₂CH(CH₃)₂ | —CO₂CH₃ |
| 2 | —CH₂CH₂CH(CH₃)₂ | 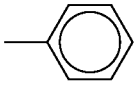 |
| 1 | 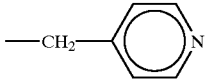 | 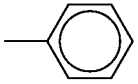 |
| 1 | 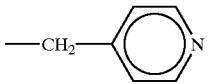 | 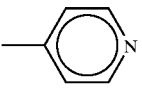 |
| 0 | —CH₂CH₂CH(CH₃)₂ | 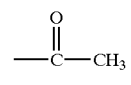 |
| 0 | 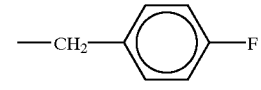 | 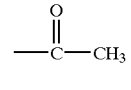 |
| 1 | 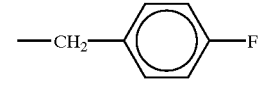 | 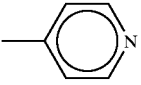 |
| 1 | —CH₂CH(CH₃)₂ | OH |
| 1 | 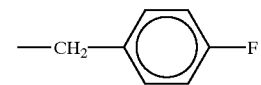 | OH |
| 2 | 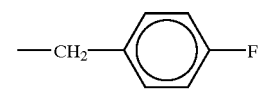 | 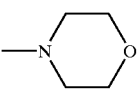 |
| 2 | 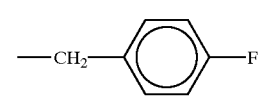 | 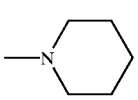 |
| 1 | 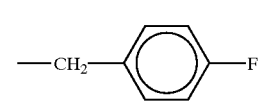 | —SCH₃ |

TABLE 12-continued

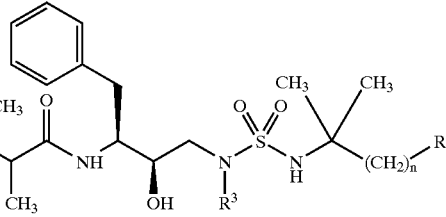

| n | R³ | R⁸ |
|---|---|---|
| 1 | —CH₂—C₆H₄—F (4-F) | —SO₂CH₃ |
| 1 | —CH₂-(4-pyridyl) | —SO₂CH₃ |
| 1 | —CH₂CH(CH₃)₂ | —CO₂CH₃ |
| 1 | —CH₂—C₆H₄—F (4-F) | —CO₂H |
| 1 | —CH₂—C₆H₄—F (4-F) | —CO₂CH₂—C₆H₄—OCH₃ |
| 1 | —CH₂—C₆H₄—F (4-F) | —SO₂Ph |
| 1 | —CH₂-(4-pyridyl) | —SO₂Ph |
| 1 | —CH₂CH₂CH(CH₃)₂ | 4-pyridyl |
| 2 | —CH₂CH₂CH(CH₃)₂ | —N(CH₃)₂ |
| 2 | —CH₂CH₂CH(CH₃)₂ | 4-methylpiperazin-1-yl |
| 1 | —CH₂CH₂CH(CH₃)₂ | morpholin-4-yl |
| 1 | —CH₂CH₂CH(CH₃)₂ | 4-methylpiperazin-1-yl |
| 1 | —CH₂CH₂CH(CH₃)₂ | piperidin-1-yl |
| 1 | —CH₂CH₂CH(CH₃)₂ | 4-methylpiperazin-1-yl |
| 1 | —CH₂CH₂CH(CH₃)₂ | —N(CH₃)Ph |

TABLE 12-continued

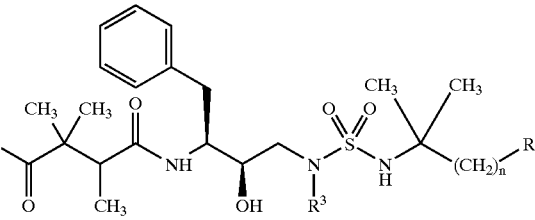

| n | R³ | R⁸ |
|---|---|---|
| 1 | —CH₂CH₂CH(CH₃)₂ |  —O—CH₂CH₂—N⟨morpholine⟩ |
| 1 | —CH₂CH₂CH(CH₃)₂ | 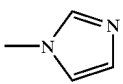 imidazolyl |

EXAMPLE 13

The compounds of the present invention are effective HIV protease inhibitors. Utilizing an enzyme assay as described below, the compounds set forth in the examples herein would be expected to inhibit the HIV enzyme. The enzyme method is described below. The substrate is 2-Ile-Nle-Phe (p-NO$_2$)-Gln-ArgNH$_2$. The positive control is MVT-101 (Miller, M. et al, Science, 246, 1149 (1989)] The assay conditions are as follows:

| Assay buffer: | 20 mM sodium phosphate, pH 6.4 |
|---|---|
| | 20% glycerol |
| | 1 mM EDTA |
| | 1 mM DTT |
| | 0.1% CHAPS |

The above described substrate is dissolved in DMSO, then diluted 10 fold in assay buffer. Final substrate concentration in the assay is 80 μM.

HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10× the test concentration; 10 μl of the enzyme preparation is added, the materials mixed and then the mixture is incubated at ambient temperature for 15 minutes. The enzyme reaction is initiated by the addition of 40 μl of substrate. The increase in fluorescence is monitored at 4 time points (0, 8, 16 and 24 minutes) at ambient temperature. Each assay is carried out in duplicate wells.

EXAMPLE 14

The effectiveness of the compounds can also be determined in a CEM cell assay.

The HIV inhibition assay method of acutely infected cells is an automated tetrazolium based colorimetric assay essentially that reported by Pauwles et al, J. Virol. Methods, 20, 309–321 (1988). Assays can be performed in 96-well tissue culture plates. CEM cells, a CD4⁺ cell line, were grown in RPMI-1640 medium (Gibco) supplemented with a 10% fetal calf serum and were then treated with polybrene (2 μg/ml). An 80 μl volume of medium containing 1×10$^4$ cells is dispensed into each well of the tissue culture plate. To each well is added a 100 μl volume of test compound dissolved in tissue culture medium (or medium without test compound as a control) to achieve the desired final concentration and the cells are incubated at 37° C. for 1 hour. A frozen culture of HIV-1 is diluted in culture medium to a concentration of 5×10$^4$ TCID$_{50}$ per ml (TCID$_{50}$=the dose of virus that infects 50% of cells in tissue culture), and a 20 μL volume of the virus sample (containing 1000 TCID$_{50}$ of virus) is added to wells containing test compound and to wells containing only medium (infected control cells). Several wells receive culture medium without virus (uninfected control cells). Likewise, the intrinsic toxicity of the test compound is determined by adding medium without virus to several wells containing test compound. In summary, the tissue culture plates contain the following experiments:

| | Virus | Cells | Drug |
|---|---|---|---|
| 1. | + | − | − |
| 2. | + | + | − |
| 3. | + | − | + |
| 4. | + | + | + |

In experiments 2 and 4 the final concentrations of test compounds are 1, 10, 100 and 500 μg/ml. Either azidothymidine (AZT) or dideoxyinosine (ddI) is included as a positive drug control. Test compounds are dissolved in DMSO and diluted into tissue culture medium so that the final DMSO concentration does not exceed 1.5% in any case. DMSO is added to all control wells at an appropriate concentration.

Following the addition of virus, cells are incubated at 37° C. in a humidified, 5% CO$_2$ atmosphere for 7 days. Test compounds could be added on days 0, 2 and 5 if desired. On day 7, post-infection, the cells in each well are resuspended and a 100 μl sample of each cell suspension is removed for assay. A 20 μL volume of a 5 mg/ml solution of 3-(4,5-dimethylthiazol-2-yl)-2,5-diphenyltetrazolium bromide (MTT) is added to each 100 μL cell suspension, and the cells are incubated for 4 hours at 27° C. in a 5% $CO_2$ environment. During this incubation, MTT is metabolically reduced by living cells resulting in the production in the cell of a colored formazan product. To each sample is added 100 μl of 10% sodium dodecylsulfate in 0.01 N HCl to lyse the cells, and samples are incubated overnight. The absorbance at 590 nm is determined for each sample using a Molecular Devices microplate reader. Absorbance values for each set of wells is compared to assess viral control infection, uninfected control cell response as well as test compound by cytotoxicity and antiviral efficacy.

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in particular other strains of HIV, e.g. HIV-2, human T-cell leukemia virus, respiratory syncitial virus, simia immunodeficiency virus, feline leukemia virus, feline immuno-deficiency virus, hepadnavirus, cytomegalovirus and picornavirus. Thus, the subject compounds are effective in the treatment and/or proplylaxis of retroviral infections.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT, DDI, DDC or with glucosidase inhibitors, such as N-butyl-1-deoxynojirimycin or prodrugs thereof, for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compound represented by the formula:

(II)

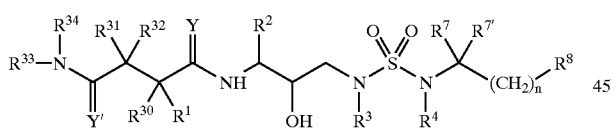

wherein:

$R^1$ represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals, and amino acid side chains selected from asparagine, S-methyl cysteine, methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-methyl serine, aspartic acid, beta-cyanoalanine and valine side chains;

$R^2$ represents alkyl, aryl, cycloalkyl, cycloalkylalkyl and aralkyl radicals, which radicals are optionally substituted with a group selected from alkyl and halogen radicals, —$NO_2$, —C≡N, $CF_3$, —$OR^9$, —$SR^9$, wherein $R^9$ represents hydrogen and alkyl radicals;

$R^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone and sulfoxide derivatives thereof;

$R^4$ represents hydrogen and radicals as defined by $R^3$;

$R^7$ and $R^{7'}$ independently represent radicals as defined for $R^3$ and amino acid side chains selected from the group consisting of valine, isoleucine, glycine, alanine, allo-isoleucine, asparagine, leucine, glutamine, and t-butylglycine or $R^7$ and $R^{7'}$ together with the carbon atom to which they are attached form a cycloalkyl radical;

$R^8$ represents cyano, hydroxyl, alkyl, alkoxy, cycloalkyl, aryl, aralkyl, heterocycloalkyl and heteroaryl radicals and radicals represented by the formulas $C(O)R^{16}$, $CO_2R^{16}$, $SO_2R^{16}$, $SR^{16}$, $CONR^{16}R^{17}$, $CF_3$ and $NR^{16}R^{17}$;

wherein $R^{16}$ and $R^{17}$ independently represent hydrogen and radicals as defined for $R^3$, or $R^{16}$ and $R^{17}$ together with a nitrogen to which they are attached in the formula $NR^{16}R^{17}$ represent heterocycloalkyl and heteroaryl radicals;

$R^{30}$, $R^{31}$ and $R^{32}$ independently represent radicals as defined for $R^1$, or one of $R^1$ and $R^{30}$ together with one of $R^{31}$ and $R^{32}$ and the carbon atoms to which they are attached form a cycloalkyl radical;

$R^{33}$ and $R^{34}$ independently represent hydrogen and radicals as defined for $R^3$, or $R^{33}$ and $R^{34}$ together with the nitrogen atom to which they are attached represent heterocycloalkyl and heteroaryl radicals;

n represents an integer of from 0 to 6; and

Y and Y' represent O.

2. Compound of claim 1 wherein $R^1$ represents hydrogen and $CH_2C(O)NHCH_3$, $C(CH_3)_2(SCH_3)$, $C(CH_3)_2(S[O]CH_3)$, $C(CH_3)_2(S[O]_2CH_3)$, alkyl, alkenyl and alkynyl radicals, and amino acid side chains selected from the group consisting of asparagine, valine, threonine, allo-threonine, isoleucine, tert-leucine, S-methyl cysteine and the sulfone and sulfoxide derivatives thereof, methionine and the sulfone and sulfoxide derivatives thereof, alanine, and allo-isoleucine;

$R^2$ represents alkyl, cycloalkylalkyl and aralkyl radicals, which radicals are optionally substituted with halogen radicals and radicals represented by the formula —$OR^9$ and —$SR^9$ wherein $R^9$ represents alkyl radicals;

$R^3$ represents alkyl, haloalkyl, thioalkyl, alkenyl, alkoxyalkyl, alkylthioalkyl, cycloalkyl, cycloalkylalkyl, heterocycloalkyl, heterocycloalkylalkyl, aryl, aralkyl and heteroaralkyl radicals;

R4 represents hydrogen, alkyl, cycloalkyl, cycloalkylalkyl, aryl, heteroaryl, aralkyl, heteroaralkyl, heterocycloalkyl and heterocycloalkylalkyl radicals;

$R^7$ and $R^{7'}$ independently represent alkyl and aralkyl radicals or together with the carbon atom to which they are attached form a cycloalkyl radical having from 3 to 8 carbon atoms;

R⁸ represents alkylcarbonyl, aryl, aroyl, aryloxy, aralkanoyl, cyano, hydroxycarbonyl, arylsulfonyl, alkylsulfonyl, alkylthio, hydroxyl, alkoxy, heteroaryl, dialkylaminocarbonyl, dialkylamino, cycloalkylamino, heterocyclylamino and alkoxycarbonyl radicals;

R³⁰, R³¹ and R³² independently represent hydrogen and alkyl, alkenyl and alkynyl radicals, or one of R¹ and R³⁰ together with one of R³¹ and R³² and the carbon atoms to which they are attached form a cycloalkyl radical;

R³³ and R³⁴ independently represent hydrogen and alkyl, alkenyl and alkynyl, hydroxyalkyl, alkoxyalkyl, cycloalkyl, cycloalkylalkyl, heterocycloalkyl, aryl, aralkyl, heteroaryl and heteroaralkyl radicals; and n is an integer of from 0 to 6.

3. Compound of claim 1 wherein R¹ represents hydrogen and CH₂C(O)NHCH₃, C(CH₃)₂(SCH₃), C(CH₃)₂(S[O]CH₃), C(CH₃)₂(S[O]₂CH₃), methyl, propargyl, t-butyl, isopropyl and sec-butyl radicals, and amino acid side chains selected from the group consisting of asparagine, valine, S-methyl cysteine, methionine, allo-iso-leucine, iso-leucine, and beta-cyano alanine side chains;

R² represents CH₃SCH₂CH₂—, iso-butyl, n-butyl, benzyl, 4-fluorobenzyl, 2-naphthylmethyl and cyclohexylmethyl radicals;

R³ represents propyl isoamyl, n-butyl, isobutyl, cyclohexyl, cyclohexylmethyl, benzyl and pyridylmethyl radicals;

R4 represents hydrogen and methyl, ethyl, i-propyl, n-propyl n-butyl, t-butyl, cyclohexyl, 1,1-dimethylpropyl and phenyl radicals;

R⁷ and R⁷' independently represent methyl, ethyl, propyl and butyl radicals, or together with the carbon atom to which they are attached form a cyclopropyl, cyclobutyl, cyclopentyl or cyclohexyl radical;

R⁸ represents methylcarbonyl, phenyl, hydroxy, methoxy, cyano, methoxycarbonyl, ethoxycarbonyl, isopropoxycarbonyl, t-butoxycarbonyl, benzyloxycarbonyl, carboxyl, methoxycarbonyl, methylsulfonyl, methylthio, phenylsulfonyl, phenyl, 2-, 3- or 4-pyridyl, 2-, 3- or 4-pyridyl N-oxide, N,N-dimethylamino, 1-piperidinyl, 4-morpholinyl, 4-(N-methyl)piperazinyl and 1-pyrrolidinyl;

R³⁰, R³¹ and R³² independently represent hydrogen and methyl, ethyl, propyl, butyl, pentyl and hexyl radicals, or one of R¹ and R³⁰ together with one of R³¹ and R³² form a cycloalkyl radical having from 3 to 8 carbon atoms;

R³³ and R³⁴ independently represent hydrogen, methyl, ethyl, propyl, butyl, pentyl and hexyl radicals, cyclohexylmethyl, cyclohexyl, benzyl and naphthylmethyl radicals; and n represents an integer of from 0 to 4.

4. A compound selected from the group consisting of:
1) 4-[3-[[[[(1-carboxyethyl)amino]sulfonyl](2-methylpropyl)amino]-2R-hydroxy-1S-(phenylmethyl)propyl]amino]-2,2,3R-trimethyl-4-oxobutanoic acid
2) 4-[3-[[[[(1-carboxy-1-methylethyl)amino]sulfonyl]-(4pyridinylmethyl)amino]-2R-hydroxy-1S-(phenylmethyl)propyl]amino]-3R-methyl-4-oxobutanoic acid
3) N-[[[3S-[(4-amino-2R,3,3-trimethyl-1,4-dioxobutyl)amino]-2R-hydroxy-4-phenylbutyl](3-methylbutyl)amino]sulfonyl]-2-methylalanine
4) 1-[[[[3S-[(4-amino-2R,3,3-trimethyl-1,4-dioxobutyl)amino]-2R-hydroxy-4-phenylbutyl](3-methylbutyl)amino]sulfonyl]amino]cyclopentanecarboxylic acid
5) phenylmethyl-4-[2R-hydroxy-3-[[[(2-hydroxy-1,1-dimethylethyl)amino]sulfonyl](2-methylpropyl)-amino]-1S-(phenylmethyl)propyl]-2,3R-dimethyl-4-oxobutanoate
6) 3-[[[[3S-[(4-amino-2R-methyl-1,4-dioxobutyl)amino]-2R-hydroxy-4-phenylbutyl](2-methylpropyl)amino]sulfonyl]amino]-3-methylbutanoic acid
7) phenylmethyl-4-[[3-[[[(1-carboxy-1-methylethyl)-methylamino]sulfonyl](2-methylpropyl)amino]-2R-hydroxy-1S-(phenylmethyl)propyl]amino]-2,2,3R-trimethyl-4-oxobutanoate
8) 4-[[3-[[[(2-carboxypropyl)amino]sulfonyl](2-methylpropyl)amino]-2R-hydroxy-1S-(phenylmethyl)propyl]amino]-2,3R-dimethyl-4-oxobutanoic acid
9) 1-[[[(4-fluorophenyl)methyl][[3S-[2R-ethyl-3,3-dimethyl-1,4-dioxo-4-(phenylmethoxy)butyl]-2R-hydroxy-4-phenylbutyl]amino]sulfonyl]amino]cyclopropanecarboxylic acid and
10) 1-[[[[2R-hydroxy-3S-[(4-methoxy-2R,3,3-trimethyl-1,4-dioxobutyl)amino]-4-phenylbutyl](3-methylbutyl)amino]sulfonyl]amino]cyclopropanecarboxylic acid.

5. A pharmaceutical composition comprising a compound of claim 1 and a pharmaceutically acceptable carrier.

6. Method of inhibiting a retroviral protease comprising administering a protease inhibiting amount of a composition of claim 5.

7. Method of claim 6 wherein the retroviral protease is HIV protease.

8. Method of treating a retroviral infection comprising administering an effective amount of a composition of claim 5.

9. Method of claim 8 wherein the retroviral infection is an HIV infection.

10. Method for treating AIDS comprising administering an effective amount of a composition of claim 5.

* * * * *